US008465752B2

(12) United States Patent
Seward

(10) Patent No.: US 8,465,752 B2
(45) Date of Patent: Jun. 18, 2013

(54) TREATMENT OF RENAL HYPERTENSION OR CAROTID SINUS SYNDROME WITH ADVENTITIAL PHARMACEUTICAL SYMPATHETIC DENERVATION OR NEUROMODULATION

(75) Inventor: Kirk Patrick Seward, San Francisco, CA (US)

(73) Assignee: Mercator Medsystems, Inc., San Leandro, CA (US)

(*) Notice: Subject to any disclaimer, the term of this patent is extended or adjusted under 35 U.S.C. 154(b) by 76 days.

(21) Appl. No.: 12/765,720

(22) Filed: Apr. 22, 2010

(65) Prior Publication Data

US 2011/0104061 A1 May 5, 2011

Related U.S. Application Data

(60) Provisional application No. 61/171,702, filed on Apr. 22, 2009, provisional application No. 61/186,704, filed on Jun. 12, 2009.

(51) Int. Cl.
*A61K 39/08* (2006.01)
*A61K 39/02* (2006.01)

(52) U.S. Cl.
USPC .............. 424/247.1; 424/236.1; 424/239.1

(58) Field of Classification Search
None
See application file for complete search history.

(56) References Cited

U.S. PATENT DOCUMENTS

| | | | |
|---|---|---|---|
| 3,780,733 A | 12/1973 | Martinez-Manzor |
| 4,105,030 A | 8/1978 | Kercso |
| 4,496,578 A | 1/1985 | Iwao et al. |
| 5,112,305 A | 5/1992 | Barath et al. |
| 5,147,294 A | 9/1992 | Smith et al. |
| 5,196,024 A | 3/1993 | Barath |
| 5,242,397 A | 9/1993 | Barath et al. |
| 5,354,279 A | 10/1994 | Hofling |
| 5,364,374 A | 11/1994 | Morrison et al. |
| 5,423,851 A | 6/1995 | Samuels |
| 5,538,504 A | 7/1996 | Linden et al. |
| 5,591,139 A | 1/1997 | Lin et al. |
| 5,609,629 A | 3/1997 | Fearnot et al. |
| 5,645,564 A | 7/1997 | Northrup et al. |
| 5,658,515 A | 8/1997 | Lee et al. |
| 5,665,071 A | 9/1997 | Wyrick |
| 5,681,281 A | 10/1997 | Vigil et al. |
| 5,693,029 A | 12/1997 | Leonhardt |
| 5,722,989 A | 3/1998 | Fitch et al. |
| 5,851,197 A | 12/1998 | Marano et al. |
| 5,879,326 A | 3/1999 | Godshall et al. |
| 6,009,877 A | 1/2000 | Edwards |
| 6,059,815 A | 5/2000 | Lee et al. |
| 6,093,172 A | 7/2000 | Funderburk et al. |
| 6,102,933 A | 8/2000 | Lee et al. |
| 6,187,210 B1 | 2/2001 | Lebouitz et al. |
| 6,210,392 B1 | 4/2001 | Vigil et al. |
| 6,256,533 B1 | 7/2001 | Yuzhakov et al. |
| 6,283,947 B1 | 9/2001 | Mirzaee |
| 6,293,925 B1 | 9/2001 | Safabash et al. |
| 6,302,870 B1 | 10/2001 | Jacobsen et al. |
| 6,331,266 B1 | 12/2001 | Powell et al. |
| 6,334,856 B1 | 1/2002 | Allen et al. |
| 6,451,240 B1 | 9/2002 | Sherman et al. |
| 6,547,803 B2 | 4/2003 | Seward et al. |
| 6,743,211 B1 | 6/2004 | Prausnitz et al. |
| 6,860,867 B2 | 3/2005 | Seward et al. |
| 6,978,174 B2 | 12/2005 | Gelfand et al. |
| 7,141,041 B2 | 11/2006 | Seward |
| 7,162,303 B2 | 1/2007 | Levin et al. |
| 7,547,294 B2 | 6/2009 | Seward et al. |
| 7,647,115 B2 | 1/2010 | Levin et al. |
| 7,666,163 B2 | 2/2010 | Seward et al. |
| 7,691,080 B2 | 4/2010 | Seward et al. |
| 7,744,584 B2 | 6/2010 | Seward et al. |
| 7,756,583 B2 | 7/2010 | Demarais et al. |
| 8,131,372 B2 | 3/2012 | Levin et al. |
| 8,145,317 B2 | 3/2012 | Demarais et al. |
| 8,150,519 B2 | 4/2012 | Demarais et al. |
| 8,150,520 B2 | 4/2012 | Demarais et al. |
| 8,184,711 B2 | 5/2012 | Horiuchi et al. |
| 2002/0050456 A1 | 5/2002 | Sheppard, Jr. et al. |

(Continued)

FOREIGN PATENT DOCUMENTS

| | | |
|---|---|---|
| JP | 05-293176 A | 11/1993 |
| JP | 11-262527 A | 9/1999 |
| JP | 2003-000708 A | 1/2003 |
| WO | WO 99/33504 A1 | 7/1999 |
| WO | WO 02/100459 A2 | 12/2002 |

OTHER PUBLICATIONS

Bilici et al (AJR, Sep. 2007, 189: W143-W145).*
Masuoka et al, Neurol. Med. Chir. (Tokyo), 2010, 50:179-182.*
Friedman, et al. Differential development of salt-induced and renal hypertension in Dahl hypertension-sensitive rats after neonatal sympathectomy. Clin Exp Hypertens. 1979;1(6):779-99.
Akinobu et al., "Effects of Renal Sympathectomy on Sodium and Water Excretion in Stroke-Prone Spontaneously Hypertensive Rats," Japan J. Pharmacol. 32, 591-597 (1982).

(Continued)

*Primary Examiner* — Nita M Minnifield
(74) *Attorney, Agent, or Firm* — Wilson, Sonsini, Goodrich & Rosati

(57) ABSTRACT

Sympathetic nerves run through the adventitia surrounding renal arteries and are critical in the modulation of systemic hypertension. Hyperactivity of these nerves can cause renal hypertension, a disease prevalent in 30-40% of the adult population. Hypertension can be treated with neuromodulating agents (such as angiotensin converting enzyme inhibitors, angiotensin II inhibitors, or aldosterone receptor blockers), but requires adherence to strict medication regimens and often does not reach target blood pressure threshold to reduce risk of major cardiovascular events. A minimally invasive solution is presented here to reduce the activity of the sympathetic nerves surrounding the renal artery by locally delivering neurotoxic or nerve-blocking agents into the adventitia. Extended elution of these agents may also be accomplished in order to tailor the therapy to the patient.

12 Claims, 11 Drawing Sheets

U.S. PATENT DOCUMENTS

| | | |
|---|---|---|
| 2002/0082543 A1 | 6/2002 | Park et al. |
| 2002/0188310 A1 | 12/2002 | Seward et al. |
| 2003/0040712 A1 | 2/2003 | Ray et al. |
| 2003/0078562 A1 | 4/2003 | Makower et al. |
| 2003/0120297 A1 | 6/2003 | Beyerlein |
| 2003/0171734 A1 | 9/2003 | Seward et al. |
| 2004/0067197 A1 | 4/2004 | Leclerc et al. |
| 2004/0138643 A1 | 7/2004 | Seward et al. |
| 2005/0021092 A1 | 1/2005 | Yun et al. |
| 2005/0090714 A1 | 4/2005 | Greff |
| 2006/0025821 A1 | 2/2006 | Gelfand et al. |
| 2006/0189941 A1 | 8/2006 | Seward et al. |
| 2006/0212076 A1 | 9/2006 | Demarais et al. |
| 2006/0212078 A1 | 9/2006 | Demarais et al. |
| 2006/0265014 A1 | 11/2006 | Demarais et al. |
| 2006/0276852 A1 | 12/2006 | Demarais et al. |
| 2007/0173899 A1 | 7/2007 | Levin et al. |
| 2007/0203549 A1 | 8/2007 | Demarais et al. |
| 2007/0269385 A1 | 11/2007 | Yun et al. |
| 2008/0004596 A1 | 1/2008 | Yun et al. |
| 2009/0076409 A1 | 3/2009 | Wu et al. |
| 2009/0232850 A1* | 9/2009 | Manack et al. ............ 424/239.1 |
| 2011/0104060 A1 | 5/2011 | Seward |

OTHER PUBLICATIONS

Bastid et al., "Percutaneous Alcoholization of the celiac plexus under echographic guidance: an alternative to splanchnicectomy? Study of 21 cases," Annales de gastroenterologie et d'hepatologie, vol. 27(4), pp. 163-166 (1991) (with English Abstract).

Bello-Reuss et al., "Effects of Acute Unilateral Renal Denervation in the Rat," Journ. of Clin. Invest., vol. 56, pp. 207-217 (1975).

Bichet et al., "Renal intracortical blood flow and rennin secretion after denervation by 6-hydroxydopamine," Canadian Journ. Phys. and Pharma., vol. 60 (2), pp. 184-192 (1982).

Bidwai et al., "Preoperative Stellate-ganglion Blockade to Prevent Hypertension Following Coronary-artery Operations," Anesthesiology, vol. 51, No. 4, pp. 345-347 (1979).

Cutts et al., "Ureteric Injury as a Complication of Chemical Sympathectomy," Eur J. Vasc Endovasc Surg 19, 212-213 (2000).

Das et al., "Sonographically Guided Coeliac Plexus Block," Clinical Radiology, 45, pp. 401-403 (1992).

Dekrey et al., "Selective Chemical Sympathectomy," Anesthesia and Analgesia, vol. 47, No. 5, (1968).

Dibona, Gerald F., L.L. Sawin, Effect of renal nerve stimulation on NaCI and H2O transport in Henle's loop of the rat,: (1982), American Physiological Society, F576-F580, 5 pages.

Dibona, Gerald F. and Linda E. Sawin, "Role of renal nerves in sodium retention of cirrhosis and congestive heart failure," Sep. 27, 1990, Am J Physiol 1991, vol. 260, © 1991 the American Physiological Society, pp. R296-R305.

Dibona, Gerald F. and Ulla C. Kopp, "Neural Control of Renal Function," Physiological Reviews Jan. 1997, vol. 77, No. 1, © 1997 American Physiological Society, pp. 75-197.

DiBona, Gerald F., "Neural Control of the Kidney—Past, Present, and Future," Nov. 4, 2002, Novartis Lecture, Hypertension 2003, vol. 41, part 2, 2002 American Heart Association, pp. 621-624.

DiBona, Gerald F., "Peripheral and Central Interactions between the Renin-Angiotensin System and the Renal Sympathetic Nerves in Control of Renal Function," Annals New York Academy of Sciences, 940:395-406 (2001).

DiBona, Gerald F., "Renal Innervation and Denervation. Lessons from Renal Transplantation Reconsidered," Artificial Organs, vol. 11, No. 6, Raven Press Ltd., © 1987 International Society for Artificial Organs, pp. 457-462.

DiBona, Gerald F., L.L. Sawin, "Effect of renal denervation on dynamic autoregulation of renal blood flow," Feb. 12, 2004, Am J Physiol Renal Physiol 286, pp. F1209-F1218.

DiBona, Gerald F., Susan Y. Jones, "Dynamic Analysis of Renal Nerve Activity Responses to Baroreceptor Denervation in Hypertensive Rats," Sep. 19, 2000, Hypertension Apr. 2001, © 2001 American Heart Association, pp. 1153-1163.

DiBona, G., "Neural Control of the Kidney: Functionally Specific Renal Sympathetic Nerve Fibers," Am J Physiol Regulatory Integrative Comp Physiol. 2000, 279: R1517-R1524, The American Physiological Society, Bethesda, MD.

DiBona, G.F., "Functionally Specific Renal Sympathetic Nerve Fibers: Role in Cardiovascular Regulation," American Journal of Hypertension, Jun. 2001, 14:163S-170S.

DiBona, G.F., "Sympathetic Nervous System and the Kidney in Hypertension," Current Opinion in Nephrology and Hypertension, 2002, 11:197-200, Lippincott Williams & Wilkins Press.

Diz et al., "Renal Denervation at Weaning Retards Development of Hypertension in New Zealand Genetically Hypertensive Rats," Hypertension, 4: 361-368 (1982).

Grady et al., "Renal blood flow varies during normal activity in conscious unrestrained rats," Am J Physiol Regul Integr Comp Physiol May 1, 1992, 262:(5) R926-R932.

Hayakawa et al., "Effect of Celiac Plexus Block and Thoracic Epidural Block on Arterial Ketone Body Ratio." *Masui*, 43(11):1653-8 (1994) (with English Abstract).

Hayakawa et al., "Paraplegia After Intraoperative Celiac Plexus Block," Anesth. Analg., 84:447-448 (1997).

Hayashi et al., "Effect of surugatoxin on celiac ganglia in cats," Folia Pharmacol. Japan, 73, pp. 657-663 (1977) (with English Abstract).

Hegedus, "Stenosis of the Celiac Artery," Radiologe 13, pp. 443-447 (1973).

Ischia et al., "Three Posterior Percutaneous Celiac Plexus Block Techniques," Anesthesiology, 76:534-540 (1992).

Janssen et al., "Effects of complete renal denervation and selective afferent renal denervation on the hypertension induced by intrarenal norepinephrine infusion in conscious rats," Journ. Hypertension 7:447-455 (1989).

Katholi et al., "Importance of the Renal Nerve in Established Two-Kidney, One Clip Goldblatt Hypertension," Hypertension, 4, pp. 166-174 (1982).

Kim et al., "Idiopathic foot dystonia treated with intramuscular phenol injection," Parkinsonism and Related Disorders , 9 (2003) pp. 355-359.

Kompanowska-Jezierska et al., "Early effects of renal denervation in the anaesthetised rat: natriuresis and increased cortical blood flow," Journ. of Physiol., 531(2), pp. 527-534 (2001).

Luippold et al., "Chronic renal denervation prevents glomerular hyperfiltration in diabetic rats," Nephrol Dial Transplant, 19, pp. 342-347 (2004).

Manjunath et al., "Management of Lower Limb Complex Regional Pain Syndrome Type 1: An Evaluation of Percutaneous Radiofrequency Thermal Lumber Sympathectomy Versus Phenol Lumbar Sympathetic Neurolysis—A Pilot Study," Anesthesia & Analgesia, vol. 106, No. 2, pp. 647-649, (2008).

Mercadante et al., "Celiac Plexus Block: A Reappraisal," Regional Anesthesia and Pain Medicine 23(1):37-48 (1998).

Moore et al., "Celiac Plexus Block: A Roentgenographic, Anatomic Study of Technique and Spread of Solution in Patients and Corpses," Anesth. Analg., vol. 60, No. 6, pp. 369-379 (1981).

Moore et al., "An Improved Technique for Celiac Plexus Block May Be More Theoretical Than Real," Anesthesiology, vol. 57, No. 4, pp. 347-348 (1982).

Myhre et al., "Monitoring of Celica Plexus Block in Chronic Pancreatitis," Pain, 38, pp. 269-274 (1989).

Norman et al., "Role of renal nerves in onset and maintenance of spontaneous hypertension," Am. J. Physiol., 243(2):H284-8 (1982).

Owitz et al., "Celiac Plexus Block: An Overview," The Mount Sinai Journal of Medicine, vol. 50, No. 6, pp. 486-490 (1983).

Ozkan et al., "Renal artery origins and variations: angiographic evaluation of 855 consecutive patients," Diagn Interv Radiol 12:183-186 (2006).

Peet, "Hypertension and its Surgical Treatment by Bilateral Supradiaphragmatic Splanchnicectomy," Amer. Journ. Surgery, vol. 74, No. 1, pp. 48-68 (1948).

Pires et al., "Renal blood flow dynamics and arterial pressure liability in the conscious rat," Hypertension, 38:147-152 (2001).

Richardson et al., "Mechanisms of Renal Release of Renin by Electrical Stimulation of the Brainstem in the Cat," Circulation Research, 34:425-434 (1974).

Skretting, "Hypotension After Intercostal Nerve Block During Thoracotomy Under General Anesthesia," Br. J. Anaesth., 53, pp. 527-529 (1981).

Smithwick, R.H., "Surgical treatment of hypertension," Am J Med (1948), 4:744-759.

Smithwick, R.H. et al., "Hypertension and associated cardiovascular disease: comparison of male and female mortality rates and their influence on selection of therapy," JAMA, 1956, 160:1023-1033.

Smithwick, R.H et al., "Splanchnicectomy for essential hypertension," Journ. Amer. Med. Assn. 1953, 152:1501-1504.

Solomon et al., Sympathetic Blockade in a Canine Model of Gram-Negative Bacterial Peritonitis, Shock, vol. 19, No. 3, pp. 215-222 (2003).

Tay et al., "Computed tomography fluoroscopy-guided chemical lumbar sympathectomy: Simple, safe and effective," Australasian Radiology, 46, pp. 163-166 (2002).

Thomas et al., "Chemical Sympathectomy Alters the Development of Hypertension in Miniature Swine," Hypertension, 17: 357-362 (1991).

Vranken et al., "Neurohistopathologic findings after a neurolytic celiac plexus block with alcohol in patients with pancreatic cancer pain,"Acta Anaesthesiol Strand, 46: 827-830 (2002).

Winternitz et al., "Role of the Renal Sympathetic Nerves in the Development and Maintenance of Hypertension in the Spontaneously Hypertensive Rat," J. Clin. Invest., vol. 66, pp. 971-978 (1980).

Altman et al., Exploring heart lymphatics in local drug delivery, Lymph. Res. Biol., (2003) 1:47-54.

Baltazar et al., "Differential contribution of syntaxin 1 and SNAP-25 to secretion in noradrenergic and adrenergic chromaffin cells," Eur J Cell Biol 2000;79(12):883-891.

BD™ PuraMatrix™ Peptide Hydrogel (Catalog No. 354250), Guidelines for Use, BD Biosciences, SPC-354250-G Rev 4.0., 2006; retrieved from the Internet: <http://www.bdbiosciences.com/external_files/dl/doc/manuals/live/web_enabled/354250Lpug.pdf>, 17 pages total.

Bokhari et al., "The enhancement of osteoblast growth and differentiation in vitro on a peptide hydrogel-polyHIPE polymer hybrid material," Biomaterials Sep. 2005;26(25):5198-5208; retrieved from the Internet: <http://web.mit.edu/lms/www/PDFpapers/Bokhari%20et%20al,%202005.pdf>.

Braun-Dullaeus et al.. "Cell cycle progression: new therapeutic target for vascular proliferative disease," Circulation. 1998; 98(1):82-9; retrieved from the Internet: <http://circ.ahajournals.org/cgi/reprint/98/1/82>.

Calhoun et al, "Resistant Hypertension: Diagnosis, Evaluation and Treatement: A scientific statement from the American Heart Association Professional Education Committee of the Council for High Blood Pressure Research," Hypertension 2008;51:1403-1419; retrieved from the Internet: <http://hyper.ahajournals.org/cgi/reprint/HYPERTENSIONAHA.108.189141v1>.

Campese et al., "Renal Afferent Denervation Prevents Hypertension in Rats with Chronic Renal Failure," Hypertension 1995;25:878-882; retrieved from the Internet: <http://hyper.ahajournals.org/cgi/content/full/25/4/878>.

Carroll et al., "Sympathetic block with botulinum toxin to treat complex regional pain syndrome," Annals of Neurology 2009;65(3):348-351.

Chan et al., "Update on Pharmacology for Restenosis," Current Interventional Cardiology Reports, 2001, 3: 149-155.

Cheng et al., "Unlabeled Uses of Botulinum Toxins: A Review, Part 1," Am J Health-Syst Pharm 2005;63(2):145-152.

Ciccone et al., "Effects of acute renal denervation on kidney function in deoxycorticosterone acetate-hypertensive swine," Hypertension 1986;8:925-931; retrieved from the Internet: <http://hyper.ahajournals.org/cgi/content/8/10/925>.

Clemens et al., "Prevention of anastomotic thrombosis by Botulinum Toxin A in an animal model," Plast Rectonstr Surg 2009;123(1) 64-70.

Connors et al, "Renal nerves mediate changes in contralateral renal blood flow after extracorporeal shockwave lithotripsy," Nephron Physiology 2003;95:67-75.

Cruickshank, Current Cardiology Reports 2003;5:441-452 (9671):1228-1230.

Daschner et al., Penetration of gentamicin into heart valves, subcutaneous and muscular tissue of patients undergoing open heart surgery, J. Cardiovasc. Surg., (1986) 581-584.

Davis et al., "Injectable self-assembling peptide nanofibers create intramyocardial microenvironments for endothelial cells," Circulation 111: 442-450, 2005; retrieved from the Internet: <http://circ.ahajournals.org/cgi/reprint/111/4/442>.

De Paiva et al, "Functional repair of motor endplates after botulinum neurotoxin type A poisoning: Biphasic switch of synaptic activity between nerve sprouts and their parent terminals," Proc Natl Acad Sci 1999;96:3200-3205; retrieved from the Internet: <http://www.pnas.org/content/96/6/3200.full.pdf+html>.

De Smet et al., "Metalloproteinase Inhibition Reduces Constrictive Arterial Remodeling After Balloon Angioplasty: A Study in the Atherosclerotic Yucatan Micropig." Circulation, 2000, 101: 2962-2967; retrieved from the Internet: <ttp://circ.ahajournals.org/cgi/reprint/101/25/2962>.

Demas et al., "Novel Method for localized, functional sympathetic nervous system denervation of peripheral tissue using guanethidine," Journal of Neuroscience Methods 2001;112:21-28.

DiBona et al., "Translational Medicine: The Antihypertensive Effect of Renal Denervation," American Journal of Physiology—Regulatory, Integrative and Comparative Physiology. Feb. 2010;298(2):R245-253.

DiBona, "Nervous Kidney: Interaction between renal sympathetic nerves and the renin-angiotensin stystem in the control of renal function," Hypertension 2000;36:1083-1088; retrieved from the Internet: <http://hyper.ahajournals.org/cgi/reprint/36/6/1083>.

DiBona, "The Sympathetic Nervous System and Hypertension: Recent Developments," Hypertension 2004;43;147-150; retrieved from the Internet: <http://hyper.ahajournals.org/cgi/reprint/43/2/147>.

Erickson et al., "Differential maturation and structure-function relationships in mesenchymal stem cell- and chondrocyte-seeded hydrogels," Tissue Engineering Part A, May 2009, 15(5): 1041-1052.

Farsak et al., "Detection of *Chlamydia pneumoniae* and *Helicobacter pylori* DNA in human atherosclerotic plaques by PCR," J Clin Microbiol 2000; 38(12):4408-4411; retrieved from the Internet: <http://jcm.asm.org/cgi/reprint/38/12/4408>.

Fassio et al., "Evidence for calcium-dependent vesicular transmitter release insensitive to tetanus toxin and botulinum toxin type F," Neuroscience 1999;90(3):893-902.

Foran et al., "Botulinum neurotoxin C1 cleaves both syntaxin and SNAP-25 in intact and permeabilized chromaffin cells: correlation with its blockade of catecholamine release," Biochemistry 1996;35(8):2630-6.

Fuchs et al., "Anti-angiogenesis: A new potential strategy to inhibit restenosis," Intl J Cardiovasc Intervent. 2001; 4:3-6.

Gallo et al., "Inhibition of intimal thickening after balloon angioplasty in porcine coronary arteries by targeting regulators of the cell cycle," Circulation. 1999; 99:2164-2170; retrieved from the Internet: <http://circ.ahajournals.org/cgi/reprint/99/16/2164>.

Grayston, "Antibiotic Treatment of *Chlamydia pneumoniae* for secondary prevention of cardiovascular events," Circulation. 1998; 97(17):1669-1670.

Grisk, "Sympatho-renal interactions in the determination of arterial pressure: role in hypertension," Experimental Physiology 2004;90(2):183-187; retrieved from the Internet: <http://ep.physoc.org/content/90/2/183.full.pdf+html>.

Healey et al., "The management of patients with carotid sinus syndrome: is pacing the answer," Clin Auton Res Oct. 2004;14 Suppl 1:80-6.

Henriksson et al., "Transplantation of human mesenchymal stems cells into intervertebral discs in a xenogeneic porcine model," Spine Jan. 15, 2009;34(2):141-8.

Herdeg et al., "Local paclitaxel delivery for the prevention of restenosis: biological effects and efficacy in vivo," J Am Coll Cardiol Jun. 2000; 35(7):1969-1976; retrieved from the Internet: <http://content.onlinejacc.org/cgi/reprint/35/7/1969.pdf>.

Huang et al., "Renal denervation prevents and reverses hyperinsulinemia-induced hypertension in rats," Hypertension 1998;32:249-254; retrieved from the Internet: <http://hyper.ahajournals.org/cgi/reprint/32/2/249>.

Humeau et al., "How botulinum and tetanus neurotoxins block neurotransmitter release," Biochimie 2000;82(5):427-446.
Ismail et al, "The role of infection in atherosclerosis and coronary artery disease: a new therapeutic target," Heart Dis. 1999; 1(4):233-240.
Joles et al., "Causes and Consequences of Increased Sympathetic Activity in Renal Disease," Hypertension 2004;43:699-706; retrieved from the Internet: <http://hyper.ahajournals.org/cgi/reprint/43/4/699>.
Katholi et al., "Role of the renal nerves in the pathogenesis of one-kidney renal hypertension in the rat," Hypertension 1981;3:404-409; retrieved from the Internet: <http://hyper.ahajournals.org/cgi/reprint/3/4/404>.
Kim et al., "A microfluidic platform for 3-dimensional cell culture and cell-based assays," Biomed Microdevices Feb. 2007;9(1):25-34.
Kol et al., "Chlamydial and human heat shock protein 60s activate human vascular endothelium, smooth muscle cells, and macrophages," J Clin Invest, 199; 103(4):571-577; retrieved from the Internet: <http://www.jci.org/articles/view/5310>, Feb. 15, 1999.
Koutsopoulos et al., "Controlled release of functional proteins through designer self-assembling peptide nanofiber hydrogel scaffold," Proc Natl Acad Sci 2009;106(12):4623-4628; retreived from the Internet: <http://www.pnas.org/content/early/2009/03/06/0807506106.full.pdf+html>.
Krum et al, "Catheter-based renal sympathetic denervation for resistant hypertension: a multicentre safety and proof-of-principle cohort study," Lancet 2009;373(9671):1228-1230.
Laham et al., Intracoronary and intravenous administration of basic fibroblast growth factor: myocardial and tissue distribution, Drug Met. Disp., (1999) 27:821-826.
Laham et al., Intrapericardial administration of basic fibroblast growth factor: myocardial and tissue distribution and comparison with intracoronary and intravenous administration, Cath Cardio. Interv., (2003) 58:375-381.
Lowe et al., "Coronary in-stent restenosis: Current status and future strategies," J Am Coll Cardiol. Jan. 16, 2002; 39(2):183-93; retrieved from the Internet: <http://content.onlinejacc.org/cgi/reprintframed/39/2/183>.
Lundemose et al., "*Chlamydia trachomatis* Mip-like protein has peptidyl-prolyl cis/trans isomerase activity that is inhibited by FK506 and rapamycin and is implicated in initiation of chlamydial infection," Mol Microbiol. 1993; 7(5):777-83.
Misawa et al., "PuraMatrix facilitates bone regeneration in bone defects of calvaria in mice," Cell Transplant 2006;15(10):903-910.
Mizelle et al, "Role of renal nerves in compensatory adaptation to chronic reductions in sodium uptake," Am J Physiol Renal Physiol, 1987; 252(2): F291-F298.
Morris et al., "Botulinum neurotoxin A attenuates release of norepinephrine but not NPY from vasoconstrictor neurons," Am J Physiol Heart Circ Physiol 2002;283(6):H2627-H2635; retrieved from the Internet: <http://ajpheart.physiology.org/cgi/reprint/283/6/H2627>.
Muhlestein et al., "Infection with *Chlamydia pneumoniae* accelerates the development of atherosclerosis and treatment with azithromycin prevents it in a rabbit model," Circulation. 1998; 97:633-636; retrieved from the Internet: <http://circ.ahajournals.org/cgi/reprint/97/7/633>.
Nagai et al., "Slow release of molecules in self-assembling peptide nanofiber scaffold," J Control Rel. 2006;115:18-25.
Nozdrachev et al., "The changes in the nervous structures under the chemical sympathectomy with guanethidine," Journal of the Autonomic Nervous System 1998;74(2-3):82-85.
Picklo, "Methods of sympathetic degeneration and alteration," Journal of the Autonomic Nervous System 1997;62:111-125.
Simpson, "Botulinum Toxin: a Deadly Poison Sheds its Negative Image," Annals of Internal Medicine 1996;125(7):616-617.

Smyth et al., "Nicotinamide adenine dinucleotide is released from sympathetic nerve terminals via a botulinum neurotoxin A-mediated mechanism in canine mesenteric artery," Am J Physiol Heart Circ Physiol 2006;290:H1818-H1825; retrieved from the Internet: <http://ajpheart.physiology.org/cgi/reprint/290/5/H1818>.
Spencer et al., "Peptide- and collagen-based hydrogel substrates for in vitro culture of chick cochleae," Biomaterials Mar. 2008;29(8):1028-1042; retrieved from the Internet: http://www.ncbi.nlm.nih.gov/pmc/articles/PMC2424202/pdf/nihms-52789.pdf>.
Thonhoff JR, et al., "Compatibility of human fetal neural stem cells with hydrogel biomaterials in vitro," Brain Res Jan. 2, 2008;1187:42-51; retrieved from the Internet: <http://www.ncbi.nlm.nih.gov/pmc/articles/PMC2176077/pdf/nihms36277.pdf>.
Toorop et al., "Effective surgical treatment of the carotid sinus sindrome," J Cardiovasc Surg (Torino). Oct. 2009;50(5):683-686. Epub Oct. 24, 2008.
Toorop et al., "Adventitial Stripping for Carotid Sinus Syndrome," Ann Vasc Surg. Jul.-Aug. 2009;23(4):538-47. Epub Jan. 8, 2009.
Varenne et al., "Gene Therapy for Coronary Restenosis: A Promising Strategy for the New Millennium?" Current Interventional Cardiology Reports, 2000, 2(4):309-315.
Villanueva et al., "Epinephrine and dopamine colocalization with norepinephrine in various peripheral tissues: guanethidine effects," Life Sci. 2003;73(13)1645-53.
Vincenzi, "Effect of Botulinum Toxin on Autonomic Nerves in a Dually Innervated Tissue," Nature 1967;213:394-395.
Wang et al., "Three-dimensional primary hepatocyte culture in synthetic self-assembling peptide hydrogel," Tissue Eng Part A Feb. 2008;14(2):227-36.
Yamaoka et al., "Cartilage tissue engineering using human auricular chondrocytes embedded in different hydrogel materials," J Biomed Mater Res A Jul. 2006;78(1):1-11; retrieved from the Internet: <http://www.puramatrix.com/publication/YamaokaEtal_BiomedMater.pdf>.
Yoshida ,"The use of 3-D culture in peptide hydrogel for analysis of discoidin domain receptor 1-collagen interaction," Cell Adh Migr, Apr. 2007;1(2):92-98; retrieved from the Internet: <http://www.ncbi.nlm.nih.gov/pmc/articles/PMC2633976/pdf/cam0102_0092.pdf>.
Zhang et al., "PuraMatrix: Self-assembling Peptide Nanofiber Scaffolds," Chapter 15 in *Scaffolding in Tissue Engineering*, CRC Press, 2005; retrieved from the Internet: <http://www.3d-matrix.co.jp/dl_file/PuraMatrix_Introduction.pdf>.
International Search Report and Written Opinion of PCT Application No. PCT/US10/32097, mailed Jun. 18, 2010, 8 pages total.
EP 10767782 Search Report dated Sep. 7, 2012.
Hengstmann et al., Europ. Journ. Clin. Pharmacol., vol. 15, pp. 121-125 (1979).
Johnson et al., "Guanethidine-Induced Destruction of Sympathetic Neurons, International Review of Neurobiology," vol. 25, p. 8-9 (Academic Press)(1984).
Krum et al., "Catheter-based renal sympathetic denervation for resistant hypertension: a multicentre safety and proof-of-principle cohort study," The Lancet, vol. 373, No. 9671, pp. 1275-1281 (2009).
Overbeck, "Pressure-independent increases in vascular resistance in hypertension: role of sympathoadrenergic influences," Hypertension, vol. 2, No. 6, pp. 780-786 (1980).
Pechan et al., "The Effect of Guanethedine and Propranolol on Capillary Blood Flow in Subcutaneous Tissue and Muscle in Essential Hypertension," Cardiology, vol. 59, No. 3, pp. 172-183 (1974).
Rahn, "The influence of renal function on plasma levels, urinary excretion, metabolism, and antihypertensive effect of guanethidine (Ismelin) in man," Clinical Nephrology, vol. 1, No. 1, pp. 14-23 (1973).
Taylor et al., "The effects of intravenous guanethidine on the systemic and pulmonary circulations in man," American Heart Journal, vol. 63, No. 2, pp. 239-264 (1962).

* cited by examiner

TREATMENT OF RENAL HYPERTENSION OR CAROTID SINUS SYNDROME WITH ADVENTITIAL PHARMACEUTICAL SYMPATHETIC DENERVATION OR NEUROMODULATION

CROSS-REFERENCES TO RELATED APPLICATIONS

This application claims the benefit of prior provisional applications 61/171,702, filed on Apr. 22, 2009 and 61/186,704, filed on Jun. 12, 2009. The full disclosures of each of these prior provisional applications are incorporated herein by reference.

BACKGROUND OF THE INVENTION

1. Field of the Invention

The present invention relates generally to medical devices, systems, and methods to treat disease. More particularly, the present invention relates to methods to treat hypertension by delivering agents to reduce hyperactive sympathetic nerve activity in the adventitia of arteries and/or veins that lead to the kidneys.

Hypertension, or high blood pressure, affects an estimated 30-40% of the world's adult population. Renal, or renovascular, hypertension can be caused by hypoperfusion of the kidneys due to a narrowing of the renal arteries. The kidneys respond by giving off hormones that signal the body to retain salt and water, causing the blood pressure to rise. The renal arteries may narrow due to arterial injury or atherosclerosis. Despite effective drug regimens to regulate the renin-angiotensin-aldosterone pathway or to remove excess fluid from the body and reduce blood pressure, some 20-30% of patients with hypertension suffer from resistant forms of the disease.

Resistant hypertension is a common clinical problem, caused when a patient is unable to control high blood pressure by systemic medication alone. Resistant hypertension is especially a problem in old and obese people. Both of these demographics are growing. While symptoms are not obvious in these patients, cardiovascular risk is greatly increased when they are unable to control their blood pressure.

Hypertension is also caused by hyperactive renal sympathetic nerves. Renal sympathetic efferent and afferent nerves run generally longitudinally along the outside of arteries leading from the aorta to the kidneys. These nerves are critically important in the initiation and maintenance of systemic hypertension. It has been shown that by severing these nerves, blood pressure can be reduced. Exemplary experiments have shown that denervation of the renal sympathetic nerves in rats with hyperinsulinemia-induced hypertension would reduce the blood pressure to normotensive levels as compared to controls [Huang W-C, et al. Hypertension 1998; 32:249-254].

Percutaneous or endoscopic interventional procedures are very common in the United States and other countries around the world. Intravascular catheter systems are used for procedures such as balloon angioplasty, stent placement, atherectomy, retrieval of blood clots, photodynamic therapy, and drug delivery. All of these procedures involve the placement of long, slender tubes known as catheters into arteries, veins, or other lumens of the body in order to provide access to the deep recesses of the body without the necessity of open surgery.

In cases where renal arterial occlusion is causing hypertension that cannot be controlled with medication, another potential therapy includes balloon angioplasty of the renal artery. In rare cases, surgical bypass grafting may be considered as a therapeutic alternative. While renal angioplasty can be effective in reducing blood pressure, angioplasty is plagued with resulting restenosis due to elastic recoil, dissection, and neointimal hyperplasia. Renal stents may improve the result, but also lead to restenosis or renarrowing of the artery due to neointimal hyperplasia.

While renal denervation had been performed with surgical methods in the past, more recently a catheter-based therapy to heat and destroy the nerves from within the renal artery using radio-frequency ablation has been studied. A human trial of the RF-ablation catheter method has also been performed, with reported reduction in blood pressure in patients enrolled in the catheter treatment arm of the study [Krum H, et al. Lancet 2009; 373(9671):1228-1230].

While the use of catheter-based radiofrequency (RF) denervation appears to have a therapeutic effect, it is unknown what long-term implications will arise from the permanent damage caused to the vessel wall and nerves by the RF procedure. Radiofrequency energy denervates the vessel by creating heat in the vessel wall. The RF probe contacts the inner lining of the artery and the RF energy is transmitted through the tissue.

Anti-hypertension therapies can be problematic in a number of respects. First, hypertension is, for the most part, an asymptomatic disease. Patients can lack compliance to medicinal regimens due to their perceived lack of symptoms. Second, even for patients that are highly compliant to drug therapy, their target blood pressure may not be reached, with little to no recourse but for intervention. Third, when intervention is taken (usually in the form of renal angioplasty and/or stenting), the long-term effects can include restenosis, progression of chronic kidney disease, and ultimately kidney failure, because angioplasty leads to activation of an injury cascade that causes fibrosis and remodeling of the target artery. Fourth, surgical techniques to bypass or denervate renal arteries are radical and can lead to a number of surgical complications. And fifth, it is unknown whether RF denervation of the artery will lead to further exacerbation of stenotic plaques, whether it is compatible with arteries in which stents have been placed, whether the energy transmission through thick plaques or fibrous intima will be enough to effect the underlying nerves procedure will work if the RF probe is in contact with a thick plaque in the majority of patients, or whether the effective deadening of not only nerves, but the smooth muscle in the arterial wall also, may lead to reactive hypervascular formation of the vasa vasorum and necrotizing plaques that, if ruptured, would result in acute kidney ischemia or chronic kidney disease. Thus, systems and protocols which are designed to produce sympathetic denervation with RF energy or surgical dissection are limited in their applicability across the breadth of hypertensive disease, or they may create new vascular complications that were not inherent to the underlying disease.

Neurotoxic agents like botulinum toxin, β-bungarotoxin (and other snake venom toxins), tetanus toxin, and α-latrotoxin, have been used or proposed for use in many surgical techniques to block nerves, reduce muscle activity or paralyze muscles. Neuromuscular blocking agents like tubocurarine, alcuronium, pipecuronium, rocuronium, pancuronium, vecuronium (and other curare-like drugs, derived originally from paralytic darts and arrows of South American tribes) have also been used to induce paralysis by competing for cholinergic receptors at the motor end-plate. The curare-like agents are short acting in comparison to the toxins. For example, botulinum toxin (which can be one of 7 different serologically distinct types, from type A to type G) have been used and is FDA approved to treat strabismus, blepharospasm, hemifacial spasm, improvement of moderate to severe frown lines (cosmetic), and for the treatment of excessive underarm sweating. Each of these uses for botulinum toxin has shown treatment effect ranging from several months to more than a year.

The lethal dose of botulinum toxin is approximately 1 ng/kg as determined by experiments in mice. Currently available forms of botulinum toxin, MYOBLOC™ and BOTOX® have specific activity of 70 to 130 U/ng and approximately 20 U/ng, respectively. One unit (1 U) is the amount of toxin found to cause death in 50% of mice tested 72 hours after intraperitoneal administration. MYOBLOC™ is available in 2500, 5000, or 10000 U vials and is prescribed for dosage totaling 2500 to 5000 U for the treatment of cervical dystonia. BOTOX® is available in 100 U per vial and is prescribed in dosages of 200-300 U for cervical dystonia, 50-75 U for axillary hyperhidrosis, or 12 U spread across 6 injections for blepharospasm. Active botulinum toxin is made up of a heavy chain and light chain with a total mass of 150 kDa; therefore, each 1 ng of active material contains approximately 4 billion active toxin molecules.

Current antihypertensive drugs typically modulate blood pressure by interrupting the renin-angiotensin-aldosterone axis or by acting as a diuretic. An earlier generation of antihypertensive agents had modes of action to directly impair the renal nervous system. Agents like guanethidine, guanacline, and bretylium tosylate would modulate hypertension by preventing release of norepinephrine (also known as noradrenaline) from sympathetic nerve terminals. With guanethidine, sympathectomy is accomplished by interfering with excitatory vesicular release and by replacing norepinephrine in synaptic vesicles. Sympathetic nerve failure has been previously demonstrated in rats and hamsters, but not humans, possibly because guanethidine was typically delivered systemically and the high local concentrations required to induce sympathetic denervation in humans would come at the risk of extremely undesirable systemic side effects. The use of guanethidine to create functional denervation in rodents is considered permanent, with no evidence of reinnervation of tissues for as long as 63 weeks after treatment in rats. In high doses, guanethidine inhibits mitochondrial respiration and leads to neuron death. Importantly for this invention, guanethidine can be used to create local denervation in a dose-dependent manner and without far-field effects. This has been seen in an experiment comparing guanethidine injection into one hindquarter of a hamster and compared to a control injection on the contralateral side, performed by Demas and Bartness, J Neurosci Methods 2001. This is an advantage for the use of the agent to localize the effect to a specific renal artery without diffusion beyond the renal sympathetic ganglion to the spinal cord or other nervous systems. Also of interest to this invention is the published observation that guanethidine selectively destroys postganglionic noradrenergic neurons (thus reducing norepinephrine) while sparing dopaminergic fibers and nonneural catecholamine-secreting cells. It is this high level of specificity for which guanethidine has been chosen as a useful therapy. Finally, guanethidine was approved by FDA for use as a systemic antihypertensive agent due to its ability to block sympathetic function, but has not been approved for local administration to cause long-term or permanent denervation.

Locally delivered guanethidine has produced localized sympathectomy in hamster hindquarters, as observed by Demas and Bartness, 2001. In a series of 10 to 20 unilateral injections of 2 microliters each containing 5 to 10 micrograms of guanethidine per microliter, into the inguinal adipose tissue of hamsters, compared to similar injections of placebo into the contralateral inguinal adipose tissue, functional sympathectomy of one side versus the other was seen with at least 200 micrograms of delivery, whether spread across 10 or 20 injections of 2 microliters each. The result was determined in this case by measuring the norepinephrine content of the tissue 2 weeks after delivery, with substantial reduction in the side that had received guanethidine versus the control (placebo) side.

Guanethidine has the chemical name Guanidine, [2-(hexahydro-1(2H)-azocinyl)ethyl]-, and is often supplied in the sulfate form, guanethidine sulfate or guanethidine monosulfate (CAS 645-43-2) with chemical name Guanidine, [2-(hexahydro-1(2H)-azocinyl)ethyl]-, sulfate (1:1). Guanethidine has been marketed under the trade name Ismelin.

Other agents have been shown to create partial or complete sympathectomy as well. These include immunosympathectomy agent anti-nerve growth factor (anti-NGF); auto-immune sympathectomy agents anti-dopamine beta-hydroxylase (anti-DβH) and anti-acetylcholinesterase (anti-AChe); chemical sympathectomy agents 6-hydroxyldopamine (6-OHDA), bretylium tosylate, guanacline, and N-(2-chloroethyl)-N-ethyl-2-bromobenzylamine (DSP4); and immunotoxin sympathectomy agents OX7-SAP, 192-SAP, anti-dopamine beta-hydroxylase saporin (DBH-SAP), and anti-dopamine beta-hydroxylase immunotoxin (DHIT). A full description of these agents is found in Picklo M J, J Autonom Nerv Sys 1997; 62:111-125. Phenol and ethanol have also been used to produce chemical sympathectomy and are also useful in the methods of this invention. Other sympatholytic agents include alpha-2-agonists such as clonidine, guanfacine, methyldopa, guanidine derivatives like betanidine, guanethidine, guanoxan, debrisoquine, guanoclor, guanazodine, guanoxabenz and the like; imadazoline receptor agonists such as moxonidine, relmenidine and the like; ganglion-blocking or nicotinic antagonists such as mecamylamine, trimethaphan and the like; MAOI inhibitors such as pargyline and the like; adrenergic uptake inhibitors such as rescinnamine, reserpine and the like; tyrosine hydroxylase inhibitors such as metirosine and the like; alpha-1 blockers such as prazosin, indoramin, trimazosin, doxazosin, urapidil and the like; non-selective alpha blockers such as phentolamine and the like; serotonin antagonists such as ketanserin and the like; and endothelin antagonists such as bosentan, ambrisentan, sitaxentan, and the like.

Additionally, agents that sclerose nerves can be used to create neurolysis or sympatholysis. Sclerosing agents that lead to the perivascular lesioning of nerves include quinacrine, chloroquine, sodium tetradecyl sulfate, ethanolamine oleate, sodium morrhuate, polidocanol, phenol, ethanol, or hypertonic solutions.

Renal sympathetic nerve activity leads to the production of norepinephrine. It has been well established that renal sympathectomy (also known as renal artery sympathectomy or renal denervation) reduces norepinephrine buildup in the kidney. This has been measured by studies that involved surgical denervation of the renal artery, published by Connors in 2004 for pigs, Mizelle in 1987 for dogs, and Katholi in 1981 for rats. In fact, it has been shown that surgical denervation of one renal artery with sham surgery on the contralateral renal artery results in reductions of approximately 90% or more in kidney norepinephrine content on the denervated side compared to the control side. This evidence of denervation is therefore used as a surrogate to test denervation methods in large animals like pigs, since these animals do not develop essential hypertension normally. Further evidence of the link between denervation and norepinephrine buildup has been presented in norepinephrine spillover from the kidney, measured in the renal vein outflow blood [as reported by Krum et al, Lancet 2009]. Further linkage has been made between the ability to reduce renal norepinephrine in large animal models (such as porcine models) indicating the ability to reduce blood pressure in hypertensive human patients.

Complete sympathectomy of the renal arteries remains problematic due to the side effects inherent with reducing blood pressure below normal levels. Over the past 30 years, an ongoing debate has taken place around the presence and impact of a "J-curve" when relating the reduction of hypertension to therapeutic benefit [Cruickshank J, Current Cardiology Reports 2003; 5:441-452]. This debate has highlighted an important point in the treatment of hypertension: that while reduction in blood pressure may reduce cardiovascular morbidity and mortality rates, too great a reduction leads to a reversal in benefit. With surgical sympathectomy, the renal efferent and afferent nerves are completely removed, so there is no ability to "titrate" the amount of sympathectomy for a given patient. An improved method is proposed here for a therapy that can be titrated to the needs of the individual patient with adventitial delivery of neurodegenerative or sympatholytic agents capable of creating dose-dependent sympathectomy. Given appropriate dose titration, therapy can be tailored to reach the bottom of the J-curve without overshooting and leading to hypotensive effects.

For all of these reasons, it would be desirable to provide additional and improved methods and kits for the adventitial/perivascular delivery of neurotoxic, sympatholytic, sympathetic nerve blocking agents or neuromuscular blocking agents (together with other agents that can modulate nerve function, neuromodulating agents) to accomplish biological and reversible denervation while not creating injury to the blood vessel or aggravating the underlying vascular disease. In particular, it would be beneficial to provide methods which specifically target therapeutic concentrations of the neuromodulating agents into the adventitia and perivascular tissue, where the sympathetic efferent and afferent nerves are located. It would be further beneficial if the methods could efficiently deliver the drugs into the targeted tissue and limit or avoid the loss of drugs into the luminal blood flow. It would be further beneficial if the methods could enhance the localization of neuromodulating agents in the adventitia and periadventitia, avoiding diffusion of agents to surrounding organs or nerves. It would be still further beneficial if the persistence of such therapeutic concentrations of the neuromodulating agents in the tissue were also increased, particularly in targeted tissues around the sympathetic nerves, including the adventitial tissue surrounding the blood vessel wall. Additionally, it would be beneficial to increase the uniformity of neuromodulating agent delivery over the desired treatment zone. Still further, it would be desirable if the tissue region or treatment zone into which the neuromodulating agent is delivered could be predicted and tracked with the use of visual imaging and positive feedback to an operating physician. At least some of these objectives will be met by the inventions described hereinafter.

2. Description of the Background Art

The following references are pertinent to intravascular and intraluminal drug delivery: O. Varenne and P. Sinnaeve, "Gene Therapy for Coronary Restenosis: A Promising Strategy for the New Millenium?" Current Interventional Cardiology Reports, 2000, 2: 309-315. B. J. de Smet, et. al., "Metalloproteinase Inhibition Reduces Constrictive Arterial Remodeling After Balloon Angioplasty: A Study in the Atherosclerotic Yucatan Micropig." Circulation, 2000, 101: 2962-2967. A. W. Chan et. al., "Update on Pharmacology for Restenosis," Current Interventional Cardiology Reports, 2001, 3: 149-155. Braun-Dullaeus R C, Mann M J, Dzau V J. Cell cycle progression: new therapeutic target for vascular proliferative disease. Circulation. 1998; 98(1):82-9. Gallo R, Padurean A, Jayaraman T, Marx S, Merce Roque M, Adelman S, Chesebro J, Fallon J, Fuster V, Marks A, Badimon J J. Inhibition of intimal thickening after balloon angioplasty in porcine coronary arteries by targeting regulators of the cell cycle. Circulation. 1999; 99:2164-2170 Herdeg C, Oberhoff M, Baumbach A, Blattner A, Axel D I, Schroder S, Heinle H, Karsch K R. Local paclitaxel delivery for the prevention of restenosis: biological effects and efficacy in vivo. J Am Coll Cardiol 2000 June; 35(7):1969-76. Ismail A, Khosravi H, Olson H. The role of infection in atherosclerosis and coronary artery disease: a new therapeutic target. Heart Dis. 1999; 1(4):233-40. Lowe H C, Oesterle S N, Khachigian L M. Coronary in-stent restenosis: Current status and future strategies. J Am Coll Cardiol. 2002 Jan. 16; 39(2):183-93. Fuchs S, Komowski R, Leon M B, Epstein S E. Anti-angiogenesis: A new potential strategy to inhibit restenosis. Intl J Cardiovasc Intervent. 2001; 4:3-6. Kol A, Bourcier T, Lichtman A H, and Libby P. Chlamydial and human heat shock protein 60 s activate human vascular endothelium, smooth muscle cells, and macrophages. J Clin Invest. 103:571-577 (1999). Farsak B, Vildirir A, Akyon Y, Pinar A, Oc M, Boke E, Kes S, and Tokgozogclu L. Detection of Chlamydia pneumoniae and Helicobacter pylori DNA in human atherosclerotic plaques by PCR. J Clin Microbiol 2000; 38(12):4408-11 Grayston J T. Antibiotic Treatment of Chlamydia pneumoniae for secondary prevention of cardiovascular events. Circulation. 1998; 97:1669-1670. Lundemose A G, Kay J E, Pearce J H. Chlamydia trachomatis Mip-like protein has peptidyl-prolyl cis/trans isomerase activity that is inhibited by FK506 and rapamycin and is implicated in initiation of chlamydial infection. Mol Microbiol. 1993; 7(5):777-83. Muhlestein J B, Anderson J L, Hammond E H, Zhao L, Trehan S, Schwobe E P, Carlquist J F. Infection with Chlamydia pneumoniae accelerates the development of atherosclerosis and treatment with azithromycin prevents it in a rabbit model. Circulation. 1998; 97:633-636. K. P. Seward, P. A. Stupar and A. P. Pisano, "Microfabricated Surgical Device," U.S. application Ser. No. 09/877,653, filed Jun. 8, 2001. K. P. Seward and A. P. Pisano, "A Method of Interventional Surgery," U.S. application Ser. No. 09/961,079, filed Sep. 20, 2001. K. P. Seward and A. P. Pisano, "A Microfabricated Surgical Device for Interventional Procedures," U.S. application Ser. No. 09/961,080, filed Sep. 20, 2001. K. P. Seward and A. P. Pisano, "A Method of Interventional Surgery," U.S. application Ser. No. 10/490,129, filed Mar. 11, 2003.

The following references are pertinent to renal denervation therapy to reduce hypertension: Calhoun D A, et al, "Resistant Hypertension: Diagnosis, Evaluation and Treatment: A scientific statement from the American Heart Association Professional Education Committee of the Council for High Blood Pressure Research," Hypertension 2008; 51:1403-1419. Campese V M, Kogosov E, "Renal Afferent Denervation Prevents Hypertension in Rats with Chronic Renal Failure," Hypertension 1995; 25:878-882. Ciccone C D and Zambraski E J, "Effects of acute renal denervation on kidney function in deoxycorticosterone acetate-hypertensive swine," Hypertension 1986; 8:925-931. Connors B A, et al, "Renal nerves mediate changes in contralateral renal blood flow after extracorporeal shockwave lithotripsy," Nephron Physiology 2003; 95:67-75. DiBona G F, "Nervous Kidney: Interaction between renal sympathetic nerves and the renin-angiotensin system in the control of renal function," Hypertension 2000; 36:1083-1088. DiBona G F, "The Sympathetic Nervous System and Hypertension: Recent Developments," Hypertension 2004; 43; 147-150. DiBona G F and Esler M, "Translational Medicine: The Antihypertensive Effect of Renal Denervation," American Journal of Physiology—Regulatory, Integrative and Comparative Physiology. 2010 February; 298(2): R245-53. Grisk O, "Sympatho-renal interactions in the determination of arterial pressure: role in hypertension," Experimental Physiology 2004; 90(2):183-187. Huang W-C, Fang T-C, Cheng J-T, "Renal denervation prevents and reverses hyperinsulinemia-induced hypertension in rats," Hypertension 1998; 32:249-254. Krum H, et al, "Catheter-based renal sympathetic denervation for resistant hypertension: a multicentre safety and proof-of-principle cohort study," Lancet 2009; 373(9671):1228-1230. Joles J A and Koomans H A, "Causes and Consequences of Increased Sympathetic Activity on Renal Disease," Hypertension 2004; 43:699-706. Katholi R E, Winternitz S R, Oparil S, "Role of the renal nerves in the pathogenesis of one-kidney renal hypertension in the rat," Hypertension 1981; 3:404-409. Mizelle H L, et al, "Role of renal nerves in compensatory adaptation to chronic reductions in sodium uptake," Am. J. Physiol. 1987; 252(Renal Fluid Electrolyte Physiol. 21): F291-F298.

The following references are pertinent to neurotoxic or neuroblocking agents: Excerpt from Simpson L L, "Botulinum Toxin: a Deadly Poison Sheds its Negative Image," Annals of Internal Medicine 1996; 125(7):616-617: "Botulinum toxin is being used to treat such disorders as strabismus, spasmodic torticollis, and loss of detrusor sphincter control. These disorders are all characterized by excessive efferent activity in cholinergic nerves. Botulinum toxin is injected near these nerves to block release of acetylcholine." Clemens M W, Higgins J P, Wilgis E F, "Prevention of anastomotic thrombosis by Botulinum Toxin A in an animal model," Plast Rectonstr Surg 2009; 123(1) 64-70. De Paiva A, et al, "Functional repair of motor endplates after botulinum neurotoxin type A poisoning: Biphasic switch of synaptic activity between nerve sprouts and their parent terminals," Proc Natl Acad Sci 1999; 96:3200-3205. Morris J L, Jobling P, Gibbins I L, "Botulinum neurotoxin A attenuates release of norepinephrine but not NPY from vasoconstrictor neurons," Am J Physiol Heart Circ Physiol 2002; 283:H2627-H2635. Humeau Y, Dousseau F, Grant N J, Poulain B, "How botulinum and tetanus neurotoxins block neurotransmitter release," Biochimie 2000; 82(5):427-446. Vincenzi F F, "Effect of Botulinum Toxin on Autonomic Nerves in a Dually Innervated Tissue," Nature 1967; 213:394-395. Carroll I, Clark J D, Mackey S, "Sympathetic block with botulinum toxin to treat complex regional pain syndrome," Annals of Neurology 2009; 65(3):348-351. Cheng C M, Chen J S, Patel R P, "Unlabeled Uses of Botulinum Toxins: A Review, Part 1," Am J Health-Syst Pharm 2005; 63(2):145-152. Fassio A, Sala R, Bonanno G, Marchi M, Raiteri M, "Evidence for calcium-dependent vesicular transmitter release insensitive to tetanus toxin and botulinum toxin type F," Neuroscience 1999; 90(3): 893-902. Baltazar G, Tomé A, Carvalho A P, Duarte E P, "Differential contribution of syntaxin 1 and SNAP-25 to secretion in noradrenergic and adrenergic chromaffin cells," Eur J Cell Biol 2000; 79(12):883-91. Smyth L M, Breen L T, Mutafova-Yambolieva V N, "Nicotinamide adenine dinucleotide is released from sympathetic nerve terminals via a botulinum neurotoxin A-mediated mechanism in canine mesenteric artery," Am J Physiol Heart Circ Physiol 2006; 290: H1818-H1825. Foran P, Lawrence G W, Shone C C, Foster K A, Dolly J O, "Botulinum neurotoxin C1 cleaves both syntaxin and SNAP-25 in intact and permeabilized chromaffin cells: correlation with its blockade of catecholamine release," Biochemistry 1996; 35(8):2630-6. Demas G E and Bartness T J, "Novel Method for localized, functional sympathetic nervous system denervation of peripheral tissue using guanethidine," Journal of Neuroscience Methods 2001; 112:21-28. Villanueva I, et al., "Epinephrine and dopamine colocalization with norepinephrine in various peripheral tissues: guanethidine effects," Life Sci. 2003; 73(13)1645-53. Picklo M J, "Methods of sympathetic degeneration and alteration," Journal of the Autonomic Nervous System 1997; 62:111-125. Nozdrachev A D, et al., "The changes in the nervous structures under the chemical sympathectomy with guanethidine," Journal of the Autonomic Nervous System 1998; 74(2-3):82-85.

The following references are pertinent to self-assembling peptide hydrogel matrix, useful to extend pharmacokinetics as described in this invention: Koutsopoulos S, Unsworth L D, Nagai Y, Zhang S, "Controlled release of functional proteins through designer self-assembling peptide nanofiber hydrogel scaffold," Proc Natl Acad Sci 2009; 106(12):4623-8. Nagai Y, Unsworth L D, Koutsopoulos S, Zhang S, "Slow release of molecules in self-assembling peptide nanofiber scaffold," J Control Rel. 2006; 115:18-25. BD™ PURAMATRIX™ Peptide Hydrogel (Catalog No. 354250) Guidelines for Use, BD Biosciences, SPC-354250-G Rev 4.0. Erickson I E, Huang A H, Chung C, Li R T, Burdick J A, Mauck R L, Tissue Engineering Part A. online publication ahead of print. doi:10.1089/ten.tea.2008.0099. Henriksson H B, Svanvik T, Jonsson M, Hagman M, Horn M, Lindahl A, Brisby H, "Transplantation of human mesenchymal stems cells into intervertebral discs in a xenogeneic porcine model," Spine 2009 Jan. 15; 34(2):141-8. Wang S, Nagrath D, Chen P C, Berthiaume F, Yarmush M L, "Three-dimensional primary hepatocyte culture in synthetic self-assembling peptide hydrogel," Tissue Eng Part A 2008 February; 14(2):227-36. Thonhoff JR, Lou D I, Jordan P M, Zhao X, Wu P, "Compatibility of human fetal neural stem cells with hydrogel biomaterials in vitro," Brain Res 2008 Jan. 2; 1187:42-51. Spencer N J, Cotanche D A, Klapperich C M, "Peptide- and collagen-based hydrogel substrates for in vitro culture of chick cochleae," Biomaterials 2008 March; 29(8):1028-42. Yoshida D, Teramoto A, "The use of 3-D culture in peptide hydrogel for analysis of discoidin domain receptor 1-collagen interaction," Cell Adh Migr 2007 April; 1(2):92-8. Kim M S, Yeon J H, Park JK, "A microfluidic platform for 3-dimensional cell culture and cell-based assays," Biomed Microdevices 2007 February; 9(1):25-34. Misawa H, Kobayashi N, Soto-Gutierrez A, Chen Y, Yoshida A, Rivas-Carrillo J D, Navarro-Alvarez N, Tanaka K, Mild A, Takei J, Ueda T, Tanaka M, Endo H, Tanaka N, Ozaki T, "PuraMatrix facilitates bone regeneration in bone defects of calvaria in mice," Cell Transplant 2006; 15(10):903-10. Yamaoka H, Asato H, Ogasawara T, Nishizawa S, Takahashi T, Nakatsuka T, Koshima I, Nakamura K, Kawaguchi H, Chung U I, Takato T, Hoshi K, "Cartilage tissue engineering using human auricular chondrocytes embedded in different hydrogel materials," J Biomed Mater Res A 2006 July; 78(1):1-11. Bokhari M A, Akay G, Zhang S, Birch M A, "The enhancement of osteoblast growth and differentiation in vitro on a peptide hydrogel-polyHIPE polymer hybrid material," Biomaterials 2005 September; 26(25):5198-208. Zhang S, Semino C, Ellis-Behnke R, Zhao X, Spirio L, "PuraMatrix: Self-assembling Peptide Nanofiber Scaffolds. Scaffolding in Tissue Engineering," CRC Press, 2005. Davis M E, Motion J P, Narmoneva D A, Takahashi T, Hakuno D, Kamm R D, Zhang S, Lee R T, "Injectable self-assembling peptide nanofibers create intramyocardial microenvironments for endothelial cells," Circulation 111: 442-450, 2005.

The following references are pertinent to carotid sinus syndrome (CSS) and adventitial denervation as a treatment option: Healey J, Connolly S J, Morillo C A, "The management of patients with carotid sinus syndrome: is pacing the answer," Clin Auton Res 2004 October; 14 Suppl 1:80-6. Toorop R J, Schelting a M R, Bender M H, Charbon J A, Huige M C, "Effective surgical treatment of the carotid sinus syndrome," J Cardiovasc Surg (Torino) 2008 Oct. 24. Toorop R J, Schelting a M R, Moll F L, "Adventitial Stripping for Carotid Sinus Syndrome," Ann Vasc Surg 2009 Jan. 7.

BRIEF SUMMARY OF THE INVENTION

Methods and kits according to the present invention are able to achieve enhanced concentrations of neuromodulating agents in targeted tissues surrounding a blood vessel, particularly adventitial tissues, more particularly renal artery and vein adventitial tissues which surround the renal sympathetic nerves. The methods rely on vascular adventitial delivery of the neuromodulating agent using a catheter having a deployable needle. The catheter is advanced intravascularly to a target injection site (which may or may not be within a renal artery) in a blood vessel. The needle is advanced through the blood vessel wall so that an aperture on the needle is positioned in adventitial tissue typically within a perivascular region (defined below) surrounding the injection site, and the neuromodulatng agent is delivered into the perivascular region through the microneedle.

This delivery protocol has been found to have a number of advantages. First, direct injection into the perivascular region has been found to immediately provide relatively high concentrations of the neuromodulating agent in the adventitial tissue immediately surrounding the injected tissue. Second, following injection, it has been found that the injected neuromodulating agents will distribute circumferentially to substantially uniformly surround the blood vessel at the injection site as well as longitudinally to reach positions which are 1 cm, 2 cm, 5 cm, or more away from the injection site, depending upon the liquid formulation in which the drug is carried. In addition, some injected neuromodulating agents may be found to distribute transmurally throughout the endothelial and intimal layers of the blood vessel, as well as in the media, or muscular layer, of the blood vessel wall. Pathways for the distribution of the neuromodulating agent are presently believed to exist through the fatty connective tissue forming the adventitia and perivascular space and may also exist in the vasa vasorum and other capillary channels through the connective tissues. Third, the delivered and distributed neuromodulating agent(s) will persist for hours or days, again depending on their carrier, their lipophilicity, and their potential to bind to cell surface receptors and undergo endocytosis. Thus, a prolonged therapeutic effect based on the neuromodulating agent may be achieved in both the adventitia and the blood vessel wall. Fourth, after the distribution has occurred, the concentration of the neuromodulating agent throughout its distribution region will be highly uniform. While the concentration of the neuromodulating agent at the injection site will always remain the highest, concentrations at other locations in the peripheral adventitia around the injection site will usually reach at least about 10% of the concentration at the injection site, often being at least about 25%, and sometimes being at least about 50%. Similarly, concentrations in the adventitia at locations longitudinally separated from the injection site by about 5 cm will usually reach at least 5% of the concentration at the injection site, often being at least 10%, and sometimes being at least 25%. Fifth, the distribution can be traced with the use of radio-contrast agents by X-ray (or by hyperechoic or hypoechoic contrast agents by ultrasound or MRI contrast agents by magnetic resonance) in order to determine the extent of diffusion, allowing one to limit the injection based on reaching a desirable diffusion region, increase the injection based on the desire to reach a greater diffusion region, or change the injection site based on an inadequate diffusion range based on the location of the needle tip, which may be embedded in a thick plaque or located intraluminally from a thick calcification. Finally, after distribution of a neuromodulating agent such as guanethidine, the agent accumulates selectively within sympathetic neurons via the amine uptake pump, and can accumulate within neurons in vivo to concentrations of 0.5 to 1.0 millimolar (mM).

The adventitial tissue surrounding arteries and veins in the body contains sympathetic nerves that provide signal pathways for the regulation of hormones and proteins secreted by the cells and organs of the body. The efferent (conducting away from the central nervous system) and afferent (conducting toward the central nervous system) sympathetic nerves that line the renal artery are held within this adventitial connective tissue. The sympathetic nervous system is responsible for up- and down-regulation of chemicals in the body that lead to homeostasis. In the case of hypertension, the sympathetic nerves that run from the spinal cord to the kidneys signal the body to produce norepinephrine at superphysiological levels, which leads to a cascade of signals causing a rise in blood pressure. Denervation of the renal arteries (and to some extent the renal veins) removes this response and allows a return to normal blood pressure.

The benefits of the present invention are achieved by delivering neuromodulating agents, such as neurotoxic, sympatholytic, sympathetic blocking agents or neuromuscular blocking agents (together and with other agents that can modulate the transmission of nerve signals) into the adventitia or perivascular region surrounding a renal artery or vein. The perivascular region is defined as the region beyond external elastic lamina of an artery or beyond the tunica media of a vein. Usually, injection will be made directly into the region of the adventitia comprised primarily of adventitial fat cells but also comprised of fibroblasts, vasa vasorum, lymphatic channels, and nerve cells, and it has been found that the neuromodulating agent disperses through the adventitia circumferentially, longitudinally, and transmurally from injection site. Such distribution can provide for delivery of therapeutically effective concentrations of the neuromodulating drugs directly to the area where nerve cells can be affected. This is difficult or impossible to accomplish with other delivery techniques (such as parenteral hypodermic needle injection).

The adventitia is a layer of fatty tissue surrounding the arteries of the human and other vertebrate cardiovascular systems. The external elastic lamina (EEL) separates the fatty adventitial tissue from muscular tissue that forms the media of the arterial wall. Needles of the present invention pass through the muscular tissue of the blood vessel and the EEL in order to reach the adventitia and perivascular space into which the drug is injected. The renal arteries or veins that are subject of this invention usually have an internal (lumen) diameter of between 1 mm and 10 mm, more often between 3 and 6 mm, particularly after angioplasty has been used to compress any plaque that may have been impinging on the lumen. The thickness of the intima and media, which separate the lumen from the EEL, are usually in the range from 200 μm to 3 mm, more often in the range from 500 μm to 1 mm. The adventitial tissue surrounding the EEL may be several millimeters thick, but the sympathetic nerves that run to the kidneys are usually within 3 mm outside the EEL, more often within 1 mm outside the EEL.

The neuromodulating agents injected in accordance with the methods described in this invention will typically either be in fluid form themselves, or will be suspended in aqueous or fluid carriers in order to permit dispersion of the neuromodulating agents through the adventitia. Drugs may also be suspended in self-assembling hydrogel carriers in order to contain the diffusion and extend the retention of agents in the area of tissue local to the injection site.

The delivery of neuromodulating agents into the adventitia outside the EEL leads to the direct targeting and interruption of the sympathetic nerve signaling pathway. With particular relevance to botulinum toxin, after delivery to the adventitia, the toxin binds with high affinity to receptors on nerve endings, and the toxin molecules penetrate the cell membrane via receptor-mediated endocytosis. Once in the nerve cell, the toxin crosses the endosome membrane by pH-dependent translocation. The toxin then reaches the cytosol, where it cleaves polypeptides that are essential for exocytosis. Without these polypeptides, incoming nerve signals cannot trigger the release of acetylcholine, thus blocking any outgoing (or transmission of) nerve signals. Botulinum toxin has been shown to block nerve activity for more than one year in humans, though recovery of the nerve signal is seen over time.

Botulinum toxins have been used primarily for their interaction with the parasympathetic nervous system, due to the toxins' ability to inhibit release of acetylcholine at the neuromuscular junction. One aspect of the present invention is to deliver a neuromodulating agent such as botulinum toxin to the adventitia of renal arteries to affect both parasympathetic and sympathetic nerves. While preganglionic sympathetic nerves are cholinergic, post-ganglionic sympathetic nerves are adrenergic, expressing noradrenaline rather than acetylcholine. It has been shown in the literature that botulinum toxin reduces the expression of noradrenaline in addition to acetylcholine, which justifies its use as a neuromodulating agent for both parasympathetic and sympathetic nervous systems as further described in this application.

There have been rare reports of cardiovascular complications with the use of botulinum neurotoxins, including myocardial infarction or arrhythmia, some with fatal outcomes. While some of these patients had cardiovascular disease risk factors and the complication may have been unrelated to the botulinum toxin injection, the release of high levels of toxin into the bloodstream or the digestive tract is worrisome due to the possibility that a patient might contract botulism.

Botulinum toxins cleave SNARE (Soluble N-sensitive factor Attachment protein REceptor) proteins, including synaptosomal-associated protein of 25-kilodaltons (SNAP-25), syntaxin, and synaptobrevin (also known as vesicle-associated membrane protein, or VAMP). Each of these proteins are required for vesicles containing acetylcholine or noradrenaline to be released from nerve cells. In this manner, botulinum toxins prevent the exocytosis of the vesicles containing catecholamines or acetylcholine. Other pathways required for the release of acetylcholine or noradrenaline can also be modified, such as the down-regulation or abolishment of any of the SNARE proteins (which, in addition to SNAP-25, syntaxin and synaptobrevin, include synaptotagmin and Rab3a). While these effects of botulinum toxin have most often been used to stop the release of acetylcholine at the neuromuscular junction to prevent muscle movement or twitch, the toxin can also be exploited to prevent signals from transmitting through the nerves in the renal artery adventitia.

The different botulinum toxin serotypes (A through G) are able to cleave different components of the SNARE complex of proteins.

While cleavage of the SNARE proteins can be accomplished with botulinum toxin, other methods may be employed to reduce or quell the hyperactive signaling in the nerves that run through the renal artery adventitia or the nerves that form other neural systems in the body. The reduction of neurotransmitters, putative neurotransmitters, or neuroactive peptides can accomplish the same goal of reducing nervous signal transmission along the renal arteries. Neurotransmitters, putative neurotransmitters, and neuroactive peptides include compounds of the amino acidergic system such as y-aminobutyrate (GABA), aspartate, glutamate, glycine, or taurine; compounds of the cholinergic system such as acetylcholine; compounds of the histaminergic system such as histamine; compounds of the monoaminergic system such as adrenaline, dopamine, noradrenaline, serotonin, or tryptamine; compounds of the peptidergic system such as angiotensin, members of the bombesin family, brakykinin, calcitonin gene related peptide (CGRP), carnosine, caerulein, members of the cholecystokinin family, corticotropin, corticotropin releasing hormone, members of the dynorphin family, eledoisin, members of the endorphin family, members of the encephalin family, members of the gastrin family, luteinizing hormone releasing hormone (LHRH), melatonin, motilin, neurokinins, members of the neuromedin family, neuropeptide K, neuropeptide Y, neurotensin, oxytocin, peptide histidine isoleucine (PHI), physalaemin, sleep inducing peptides, somatostatin, substance K, substance P, thyroid hormone releasing hormone (TRH), vasoactive intestinal peptide (VIP), or vasopressin; compounds of the purinergic system such as adenosine, ADP, AMP, or ATP; or compounds in the form of gaseous neurotransmitters such as carbon monoxide or nitric oxide.

Neural block may be accomplished with agents such as lidocaine or bupivacaine, and it has been reported that neural block may be extended with the co-injection of botulinum toxin and bupivacaine versus the toxin alone or the bupivacaine alone. The combination of agents can lead to an enhanced result because agents like bupivacaine block the influx of sodium ions into nerves, which serves to decrease action potential and nerve firing. This can also be accomplished with co-injection of toxin with calcium-channel blockers.

Sympathectomy may be accomplished with immunosympathectomy agents such as anti-nerve growth factor (anti-NGF); auto-immune sympathectomy agents such as anti-dopamine beta-hydroxylase (anti-DβH) and anti-acetylcholinesterase (anti-AChe); chemical sympathectomy agents such as 6-hydroxydopamine (6-OHDA), phenol, ethanol, bretylium tosylate, guanethidine, guanacline, and N-(2-chloroethyl)-N-ethyl-2-bromobenzylamine (DSP4); immunotoxin sympathectomy agents such as OX7-SAP, 192-SAP, anti-dopamine beta-hydroxylase saporin (DBH-SAP), and anti-dopamine beta-hydroxylase immunotoxin (DHIT); or combinations thereof. Other sympatholytic agents include alpha-2-agonists such as clonidine, guanfacine, methyldopa, guanidine derivatives like betanidine, guanethidine, guanoxan, debrisoquine, guanoclor, guanazodine, guanoxabenz, guanidine, guanadrel and the like; imadazoline receptor agonists such as moxonidine, relmenidine and the like; ganglion-blocking or nicotinic antagonists such as mecamylamine, trimethaphan and the like; MAOI inhibitors such as pargyline and the like; adrenergic uptake inhibitors such as rescinnamine, reserpine and the like; tyrosine hydroxylase inhibitors such as metirosine and the like; alpha-1 blockers such as prazosin, indoramin, trimazosin, doxazosin, urapidil and the like; non-selective alpha blockers such as phentolamine and the like; serotonin antagonists such as ketanserin and the like; endothelin antagonists such as bosentan, ambrisentan, sitaxentan, and the like; and sclerotherapeutic agents such as quinacrine, chloroquine, sodium tetradecyl sulfate, ethanolamine oleate, sodium morrhuate, polidocanol, phenol, ethanol, or hypertonic solutions.

In the case of guanethidine, systemic administration with chronic, high doses can cause functional sympathectomy, but at the expense of terrible side effects. Guanethidine causes sympathectomy by preventing the release of norepinephrine from sympathetic nerve terminals by interfering with the excitatory release of vesicles carrying norepinephrine, by replacing noradrenaline in the synaptic vesicles, by inhibiting oxidative phosphorylation in mitochondria with an effective dose in 50% of cells ($ED_{50}$) of 0.5 to 0.9 mM, by inhibiting retrograde transport of trophic factors such as nerve growth factor, and also by exerting cytotoxic effects by an immune-mediated mechanism.

In addition to chemical sympatholysis, additional methods of sympathectomy can be achieved such as by heating the nerves to within the range from 42° C. to 50° C.

In a first aspect of the present invention, a method for distributing a neuromodulating agent or combination of agents into the adventitial tissue and nerves surrounding a living vertebrate host's renal artery, such as a human renal artery, comprises positioning a microneedle through the wall of a renal blood vessel and delivering an amount of the neuromodulating agent or combination of agents therethrough.

The microneedle is inserted, preferably in a substantially normal direction, into the wall of a vessel (artery or vein) to eliminate as much trauma to the patient as possible. Until the microneedle is at the site of an injection, it is positioned out of the way so that it does not scrape against arterial or venous walls with its tip. Specifically, the microneedle remains enclosed in the walls of an actuator or sheath attached to a catheter so that it will not injure the patient during intervention or the physician during handling. When the injection site is reached, movement of the actuator along the vessel terminated, and the actuator is operated to cause the microneedle to be thrust outwardly, substantially perpendicular to the central axis of a vessel, for instance, in which the catheter has been inserted.

The aperture of the microneedle will be positioned so that it lies beyond the external elastic lamina (EEL) of the blood vessel wall and into the perivascular region surrounding the wall. Usually, the aperture will be positioned at a distance from the inner wall of the blood vessel which is equal to at least 10% of the mean luminal diameter of the blood vessel at the injection site. Preferably, the distance will be in the range from 10% to 75% of the mean luminal diameter.

When the aperture of the microneedle is located in the tissue outside of the EEL surrounding the blood vessel, the neuromodulating agent or combination of agents are delivered through the needle aperture, at which point the agent or combination distributes substantially completely circumferentially through adventitial tissue surrounding the blood vessel at the site of the microneedle. Usually, the agent will further distribute longitudinally along the blood vessel over a distance of at least 1 to 2 cm, and can extend to greater distances depending on dosage (volume) injected, within a time period no greater than 60 minutes, often within 5 minutes or less. While the concentration of the neuromodulating agent in the adventitia will decrease in the longitudinal direction somewhat; usually, the concentration measured at a distance of 2 cm from the injection site will usually be at least 5% of the concentration measured at the same time at the injection site, often being at least 10%, frequently being as much as 25%, and sometimes being as much as 50%. The concentration profile is greatly dependent on the size of the molecule or particle delivered into the adventitial and perivascular tissue. The concentration profile can be further tailored by the use of different carriers and excipients within the liquid or gel formulation in which the agent is carried.

In a second aspect of the present invention, the location of the aperture may be detected in advance of placing the full dose of neuromodulating agent into the adventitia by the use of, for example, X-ray, ultrasonic, or magnetic resonance imaging of a radio-contrast agent. The contrast agent may be delivered at the same time as the therapeutic agent, either in or out of solution with the therapeutic agent, or it may be delivered prior to the therapeutic agent to detect and confirm that the needle aperture is in the desirable tissue location outside the EEL. After determining the successful placement of the needle aperture, continued injection can be made through the needle under image guidance. Such methods for delivering agents provide the physician a positive visual feedback as to the location of the injection and diffusion range, and also to titrate the dose based on diffusion range and physiological response. The amounts of the agents delivered into the perivascular region may vary considerably, but imaging agents delivered before the therapeutic agent will usually be in the range of 10 to 200 µl, and often will be in the range of 50 to 100 µl. Therapeutic agent injection will then typically be in the range from 10 µl to 10 ml, more usually being from 100 µl to 5 ml, and often being from 500 µl to 3 ml.

In a third aspect of the present invention, methods for treatment of hypertension comprise positioning a microneedle through the wall of a renal artery or vein and delivering an effective dose of botulinum toxin to the adventitia surrounding vessels leading from the aorta to the kidney or from the kidney to the vena cava. A therapeutic effective dose of botulinum toxin to reduce neurotransmission and thereby reduce blood pressure can be monitored by the operating physician and titrated based on patient characteristics. This dose may be in the range from 10 pg (corresponding to approximately 0.2 U of BOTOX® or 1 U of MYOBLOC™) to 25 ng (corresponding to approximately 500 U of BOTOX® or 2500 U of MYOBLOC™), more usually being from 50 pg (corresponding to approximately 1 U of BOTOX® or 5 U of MYOBLOC™) to 10 ng (corresponding to approximately 200 U of BOTOX® or 1000 U of MYOBLOC™), and even more usually being from 100 pg (corresponding to approximately 2 U of BOTOX® or 10 U of MYOBLOC™) to 2.5 ng (corresponding to approximately 50 U of BOTOX® or 250 U of MYOBLOC™).

In a fourth aspect of the present invention, methods for treatment of hypertension comprise positioning a microneedle through the wall of a renal artery or vein and delivering an effective dose of guanethidine to the adventitia surrounding such vessels leading from the aorta to the kidney or from the kidney to the vena cava. A therapeutic effective dose of guanethidine to create sympathectomy and reduce norepinephrine release, thereby reducing blood pressure can be monitored by the operating physician and titrated based on patient characteristics. This dose may be in the range from 10 µg to 200 mg, usually 50 µg to 100 mg, more usually being from 100 µg to 50 mg, and even more usually being from 500 µg to 30 mg, and sometimes being from 500 µg to 10 mg.

In a fifth aspect of the present invention, methods for extending the activity of neuromodulating agents in target tissues comprises the use of agents that are endocytosed by nerve cells and then remain in the cells for long periods of time before becoming inactive.

In a sixth aspect of the present invention, methods for extending the activity of neuromodulating agents in target tissues comprises the delivery of such agents within a hydrogel that has a capacity for self assembly, such as a self-assembling peptide hydrogel matrix. When co-administered with the hydrogel material, molecules of the active agent are trapped in a nanofiber matrix as the hydrogel self-assembles due to contact with physiologic conditions. The hydrogel matrix may have fibers with diameter from 1 to 100 nm, for example, and pores with diameter from 1 to 300 nm, for example. Molecules trapped within the matrix may slowly diffuse through the porous structure or remain trapped within pores. The matrix may be slowly resorbed by the surrounding tissue, as peptide matrices are commonly known to do, and become simple amino acids. As the matrix is resorbed, trapped molecules of the active agent are then released into the surrounding tissues, leading to an ability to extend the pharmacokinetics of the neuromodulating agents. This is particularly useful with agents that do not remain active within cells for extended times. Desirable pharmacokinetic profiles are in the range of weeks to months or even years.

An exemplary hydrogel for use with the methods described in this invention is a self-assembling peptide hydrogel that comprises alternating hydrophilic and hydrophobic amino acids which, in the presence of physiological conditions, will spontaneously self-organize into an interwoven nanofiber matrix with fiber diameters of 10-20 nm. In the presence of proteins and small molecules, the nanofiber matrix traps the bioactive molecules within pores ranging from 5 to 200 nm. This self-assembling peptide, acetyl-(Arg-Ala-Asp-Ala)$_4$-CONH$_2$[Ac-(RADA)$_4$-CONH$_2$] (PURAMATRIX™), has been reported as an efficient slow-delivery carrier of small molecules. The release of proteins from the nanofiber matrix has been shown to include at least two phases. The first is a "burst" of released material, wherein it has been theorized that the protein material that is loosely trapped within large pores diffuses out rapidly (over a period of several hours), then a slower release of more tightly trapped material occurs over at least several days and is governed by Brownian motion of the proteins moving through the tight matrix. A third aspect to the release kinetics is the breakdown of the peptide matrix at its boundary, thus a release of trapped protein as the peptide is resorbed by surrounding tissue. One of the advantages of the peptide hydrogel as compared to "traditional" hydrogels is that the breakdown of the peptide structure results only in amino acid byproducts, which are easily metabolized by the body. PURAMATRIX™ is available from BD Bioscience as BD™ PURAMATRIX™ Peptide Hydrogel for research use only in 1% concentration. It is used primarily as a cell culture agent, but with application for in vivo use in the delivery of cells and bioactive agents. PURAMATRIX™ has been studied for its uses as a matrix for engineering cartilage using mesenchymal cells and chondrocytes, as a carrier of mesenchymal cells for spinal disc injury, as a hepatocyte culture matrix, to support differentiation of human fetal neural stem cells in vitro, and other cell culture and regenerative medical applications. Biocompatibility studies of PURAMATRIX™ have shown that it integrates well with tissue, much like other extracellular matrix structures, and can be resorbed over a period of several weeks. It has also been shown that functional vascular structures can be seen in the nanofiber microenvironments by 28 days after injection. With specific relevance to this invention, PURAMATRIX™ has also been shown to have no deleterious effect on the proteins that it entraps or elutes over time.

In yet another aspect of the present invention, methods to treat other diseases resulting from hyperactivity of sympathetic and parasympathetic nerves comprise delivery of neuoromodulating agents for the chemical or neuromodulating denervation of arteries. While this therapy may most often be applied to renal arteries, other vascular beds can benefit from these methods. For example, denervation of the carotid artery can be used to treat patients with carotid sinus syndrome (CSS), a condition that leads to dizziness and syncope, but can be rectified by carotid adventitial denervation.

In yet another aspect of the present invention, a method for treating vascular disease comprises the delivery of neuromodulating agents to the adventitia around blood vessels. The development of atherosclerosis, vulnerable plaques, and the growth of hyperplastic neointima have each been shown to rely on parasympathetic and sympathetic nerve signaling pathways. When interrupted, these signal pathways no longer produce the agents that end up causing the vascular inflammation that results in mortality and morbidity from associated ischemic complications.

Exemplary neuromodulating agents for creating chemical or neuromodulating denervation of renal arteries or other blood vessels in the body include neurotoxins such as botulinum toxin (serotypes A through G), resinoferatoxin, alpha-bungarotoxin, beta-bungarotoxin, tetrodotoxin, tetanus toxin, alpha-latrotoxin, tetraethylammonium, and the like; neuromuscular blocking agents like tubocurarine, alcuronium, pipecuronium, rocuronium, pancuronium, vecuronium, and the like; calcium channel blockers such as amlodipine, diltiazem, felodipine, isradipine, nicardipine, nifedipine, nisoldipine, verapamil, and the like; sodium channel blockers such as moricizine, propafenone, encainide, flecainine, tocainide, mexiletine, phenytoine, lidocaine, disopyramine, quinidine, procainamide, and the like; beta-adrenergic inhibitors such as acebutolol, atenolol, betaxolol, bisoprolol, carvedilol, esmolol, labetalol, metoprolol, nadolol, nebivolol, propranolol, pindolol, sotalol, timolol, and the like; acetylcholine receptor inhibitors such as atropine and the like, immunosympathectomy agents such as anti-nerve growth factor (anti-NGF) and the like; auto-immune sympathectomy agents such as anti-dopamine beta-hydroxylase (anti-DβH), anti-acetylcholinesterase (anti-AChe) and the like; chemical sympathectomy agents such as 6-hydroxydopamine (6-OHDA), phenol, ethanol, bretylium tosylate, guanidinium compounds (e.g. guanethidine or guanacline), N-(2-chloroethyl)-N-ethyl-2-bromobenzylamine (DSP4) and the like; immunotoxin sympathectomy agents such as OX7-SAP, 192-SAP, anti-dopamine beta-hydroxylase saporin (DBH-SAP), anti-dopamine beta-hydroxylase immunotoxin (DHIT) and the like; or combinations thereof.

One particular advantage of this invention is the ability to reverse the therapy in the case that a patient responds poorly to renal denervation. For example, if toxins are used to reduce neurotransmission, anti-toxins can be delivered (either systemically or locally) to reverse the effect and improve the patient's health. Other methods for renal sympathetic denervation have relied on surgical cutting of nerves or radiofrequency energy transmission to nerves to cause damage beyond which the nerves cannot transmit signals. Each of these previous methods is irreversible (though the RF energy transmission can lead to non-permanent effects that may wear off after months to years). If patients respond poorly to either the surgical or RF denervation procedures, there is therefore little recourse.

Another particular advantage of this invention is that side effects are limited by the very low doses that lead to therapeutic effect, often in the range from 0.1 to 2.5 ng in the case of botulinum neurotoxin or often less than 5 mg of guanethidine (whereas systemic doses of 5-50 mg/kg/day do not produce reliable sympathectomy in humans), because the methods described in this invention allow precise targeting of neuromodulators into the tissue in which the sympathetic nerves are located.

Another particular advantage of this invention is that the neuromodulating agents delivered into the adventitia according to the methods described above do not lead to death of smooth muscle cells, inflammation, or restenosis, all of which can result from radiofrequency energy transmission into arterial walls from an endoluminal aspect. Rather, the agents directly target the sympathetic and parasympathetic nerves that run through the adventitia, leaving the smooth muscle and endothelium of the vessel in a functional state, healthy and able to respond to physiological signals coming from the blood or lymph traveling around and through the vessel.

Another particular advantage of this invention is that the neuromodulating agents can be tracked during their delivery by the use of contrast agents. This allows physicians to ensure that large enough doses are given to fully treat the adventitia, but small enough doses are used such that the diffusion is limited to the area of anatomical interest This limits the potential for neuromodulating agents to reach the central nervous system. The use of imaging agents in coordination with blood pressure monitoring allows physicians to actively monitor the effect of the dose while controlling the treatment range so as not to influence surrounding tissues or nervous systems.

In still further aspects of the present invention, kits for delivering neuromodulating agents to a patient suffering from hypertension comprise a catheter, instructions for use of the catheter, and instructions for delivery of the agent. The catheter has a microneedle which can be advanced from a blood vessel lumen through a wall of the blood vessel to position an aperture of the microneedle at a perivascular space surrounding the blood vessel. The instructions for use set forth any of the exemplary treatment protocols described above. The kit may also include one or more stents and one or more angioplasty balloons that can be used to open the renal arteries and improve blood flow to the kidneys.

In a further aspect of the present invention, kits for delivering neuromodulating agents to the vascular adventitia of patients suffering from disease comprise a catheter, a neuromodulating agent which may or may not be in formulation with a carrier that can extend the elution kinetics of the agent into adventitial and adjacent tissues, instructions for use of the catheter, and dosage guidelines for the agent. The catheter has a microneedle which can be advanced from a blood vessel lumen through the wall of the blood vessel to position an aperture of the microneedle at a location outside the EEL of the blood vessel in the perivascular tissue or adventitia. The agent will usually be able to distribute circumferentially and longitudinally in the perivascular space and adventitia surrounding the blood vessel over a distance of at least 1 cm within a time of no greater than 5 minutes, usually within 1 minute or less. The instructions for use set forth any of the exemplary treatment protocols described above. The kit may also include one or more stents and one or more angioplasty balloons that can be used to open the renal arteries and improve blood flow to the kidneys.

The present invention provides methods that are enhanced by catheters that place a needle aperture outside the EEL of a blood vessel by deploying the needle from the inside of the vessel. These catheters may take on various forms. In one exemplary embodiment, a balloon or inflatable actuator is inflated to unfurl a balloon from around a microneedle that his inserted roughly perpendicularly through the vessel wall, as further described in commonly owned U.S. Pat. Nos. 6,547,803; 7,547,294; and 7,666,163. Another such exemplary embodiment employs a balloon that inflates and translates a needle and extrudes the needle tip along a path into the vessel wall. Such an exemplary embodiment has been shown with commonly owned U.S. Pat. No. 7,141,041. In each of these exemplary embodiments, multiple components may be combined into the same balloon or pressure component, such that one part of the wall is non-distensible and another part of the wall is compliant or elastomeric, such that a single inflation step, whether it involves volume or pressure, may be useful to activate both the non-distensible and compliant structures simultaneously or in series. Such enhanced embodiments for delivery catheters are described in U.S. Pat. No. 7,691,080. Exemplary methods which can be used for delivering neuromodulating agents into the adventitia are described in copending commonly owned application Ser. No. 10/691,119. The full disclosure of each of these commonly owned patents and applications are incorporated herein by reference.

It is recognized that the use of these devices and techniques to deliver to the adventitia around renal arteries is useful in the treatment of hypertension, it is also evident that the use of these devices and techniques can be applied to other arteries, such as the carotid artery, to accomplish similar goals.

BRIEF DESCRIPTION OF THE DRAWINGS

FIG. 1A is a schematic, perspective view of an intraluminal injection catheter suitable for use in the methods and systems of the present invention.

FIG. 1B is a cross-sectional view along line 1B-1B of FIG. 1A.

FIG. 1C is a cross-sectional view along line 1C-1C of FIG. 1A.

FIG. 2A is a schematic, perspective view of the catheter of FIGS. 1A-1C shown with the injection needle deployed.

FIG. 2B is a cross-sectional view along line 2B-2B of FIG. 2A.

FIG. 3 is a schematic, perspective view of the intraluminal catheter of FIGS. 1A-1C injecting therapeutic agents into an adventitial space surrounding a body lumen in accordance with the methods of the present invention.

FIGS. 4A-4D are cross-sectional views of the inflation process of an intraluminal injection catheter useful in the methods of the present invention.

FIGS. 5A-5C are cross-sectional views of the inflated intraluminal injection catheter useful in the methods of the present invention, illustrating the ability to treat multiple lumen diameters.

FIG. 6 is a perspective view of a needle injection catheter useful in the methods and systems of the present invention.

FIG. 7 is a cross-sectional view of the catheter FIG. 6 shown with the injection needle in a retracted configuration.

FIG. 8 is a cross-sectional view similar to FIG. 7, shown with the injection needle laterally advanced into luminal tissue for the delivery of therapeutic or diagnostic agents according to the present invention.

FIG. 9 is a schematic illustration of an artery together with surrounding tissue illustrating the relationship between the perivascular tissue, the adventitia, and the blood vessel wall components.

FIG. 10A is a schematic illustration of the kidney and arterial structure that brings blood to the kidney.

FIG. 10B is a schematic illustration of FIG. 10A with sympathetic nerves shown leading from the aorta around the renal artery to the kidney.

DETAILED DESCRIPTION OF THE INVENTION

The present invention will preferably utilize microfabricated catheters for intravascular injection. The following description and FIGS. 1-8 provide three representative embodiments of catheters having microneedles suitable for the delivery of a neuromodulating agent into a perivascular space or adventitial tissue. A more complete description of the catheters and methods for their fabrication is provided in U.S. Pat. Nos. 7,141,041; 6,547,803; 7,547,294; 7,666,163 and 7,691,080, the full disclosures of which have been incorporated herein by reference.

The present invention describes methods and kits useful for the delivery of neuromodulating agents into the adventitia around renal arteries in order to reduce blood pressure in the treatment of hypertension. In each kit, a delivery catheter may be combined with instructions for use and a therapeutically effective amount of a neuromodulating agent as defined above.

Figure 1A:
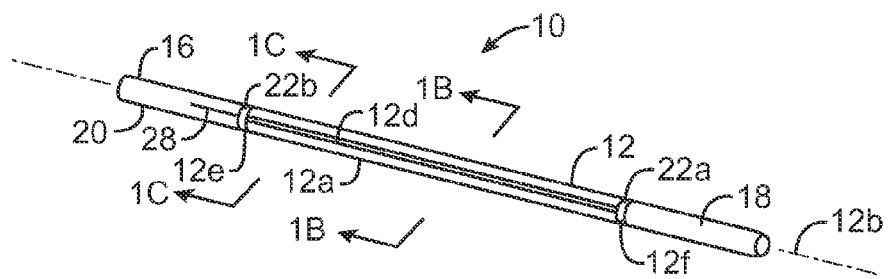
Figure 1B:
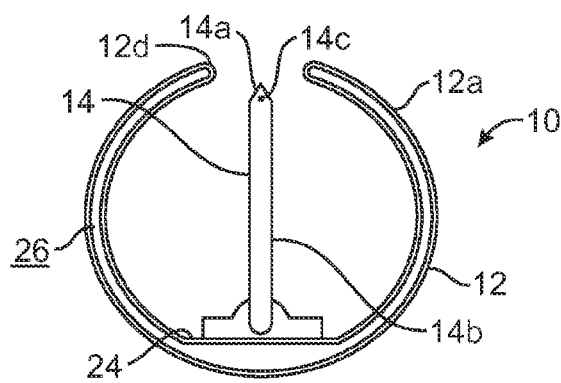
Figure 1C:
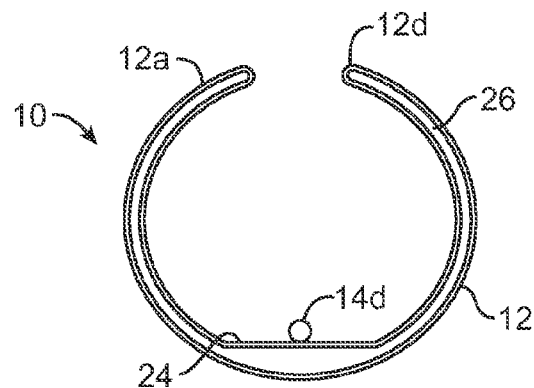
Figure 2A:
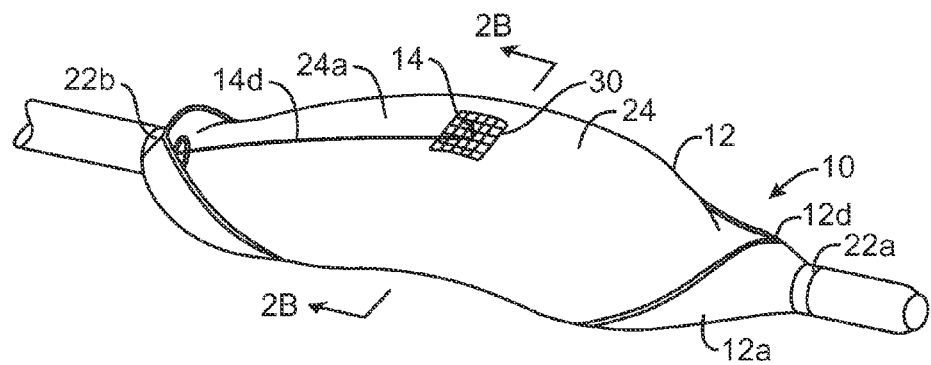
Figure 2B:
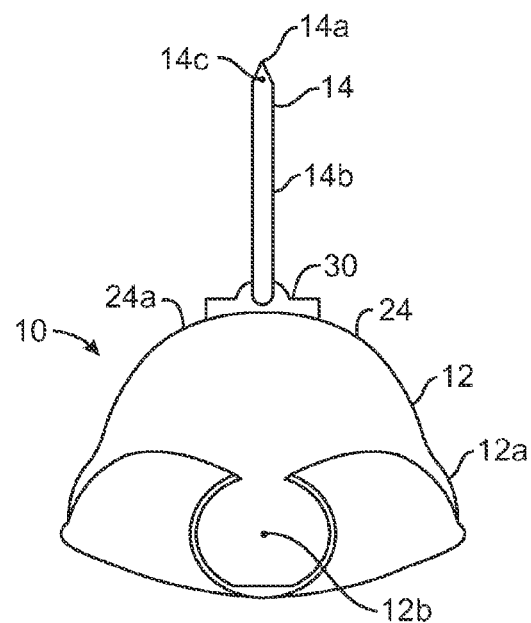

As shown in FIGS. 1A-2B, a microfabricated intraluminal catheter 10 includes an actuator 12 having an actuator body 12a and central longitudinal axis 12b. The actuator body more or less forms a U-shaped or C-shaped outline having an opening or slit 12d extending substantially along its length. A microneedle 14 is located within the actuator body, as discussed in more detail below, when the actuator is in its unactuated condition (furled state) (FIG. 1B). The microneedle is moved outside the actuator body when the actuator is operated to be in its actuated condition (unfurled state) (FIG. 2B).

The actuator may be capped at its proximal end 12e and distal end 12f by a lead end 16 and a tip end 18, respectively, of a therapeutic catheter 20. The catheter tip end serves as a means of locating the actuator inside a body lumen by use of a radio opaque coatings or markers. The catheter tip also forms a seal at the distal end 12f of the actuator. The lead end of the catheter provides the necessary interconnects (fluidic, mechanical, electrical or optical) at the proximal end 12e of the actuator.

Retaining rings 22a and 22b are located at the distal and proximal ends, respectively, of the actuator. The catheter tip is joined to the retaining ring 22a, while the catheter lead is joined to retaining ring 22b. The retaining rings are made of a thin, on the order of 10 to 100 microns (μm), substantially flexible but relatively non-distensible material, such as Parylene (types C, D or N), or a metal, for example, aluminum, stainless steel, gold, titanium or tungsten. The retaining rings form a flexible but relatively non-distensible substantially "U"-shaped or "C"-shaped structure at each end of the actuator. The catheter may be joined to the retaining rings by, for example, a butt-weld, an ultra sonic weld, integral polymer encapsulation or an adhesive such as an epoxy or cyanoacrylate.

The actuator body further comprises a central, expandable section 24 located between retaining rings 22a and 22b. The expandable section 24 includes an interior open area 26 for rapid expansion when an activating fluid is supplied to that area. The central section 24 is made of a thin, semi-flexible but relatively non-distensible or flexible but relatively non-distensible, expandable material, such as a polymer, for instance, Parylene (types C, D or N), silicone, polyurethane or polyimide. The central section 24, upon actuation, is expandable somewhat like a balloon-device.

The central section is capable of withstanding pressures of up to about 200 psi upon application of the activating fluid to the open area 26. The material from which the central section is made of is flexible but relatively non-distensible or semi-flexible but relatively non-distensible in that the central section returns substantially to its original configuration and orientation (the unactuated condition) when the activating fluid is removed from the open area 26. Thus, in this sense, the central section is very much unlike a balloon which has no inherently stable structure.

The open area 26 of the actuator is connected to a delivery conduit, tube or fluid pathway 28 that extends from the catheter's lead end to the actuator's proximal end. The activating fluid is supplied to the open area via the delivery tube. The delivery tube may be constructed of Teflon© or other inert plastics. The activating fluid may be a saline solution or a radio-opaque dye.

The microneedle 14 may be located approximately in the middle of the central section 24. However, as discussed below, this is not necessary, especially when multiple microneedles are used. The microneedle is affixed to an exterior surface 24a of the central section. The microneedle is affixed to the surface 24a by an adhesive, such as cyanoacrylate. Alternatively, the microneedle maybe joined to the surface 24a by a metallic or polymer mesh-like structure 30 (See FIG. 2A), which is itself affixed to the surface 24a by an adhesive. The mesh-like structure may be-made of, for instance, steel or nylon.

The microneedle includes a sharp tip 14a and a shaft 14b. The microneedle tip can provide an insertion edge or point. The shaft 14b can be hollow and the tip can have an outlet port 14c, permitting the injection of a neuromodulating or drug into a patient. The microneedle, however, does not need to be hollow, as it may be configured like a neural probe to accomplish other tasks. As shown, the microneedle extends approximately perpendicularly from surface 24a. Thus, as described, the microneedle will move substantially perpendicularly to an axis of a lumen into which has been inserted, to allow direct puncture or breach of body lumen walls.

The microneedle further includes a neuromodulating or drug supply conduit, tube or fluid pathway 14d which places the microneedle in fluid communication with the appropriate fluid interconnect at the catheter lead end. This supply tube may be formed integrally with the shaft 14b, or it may be formed as a separate piece that is later joined to the shaft by, for example, an adhesive such as an epoxy. The microneedle 14 may be bonded to the supply tube with, for example, an adhesive such as cyanoacrylate.

The needle 14 may be a 30-gauge, or smaller, steel needle. Alternatively, the microneedle may be microfabricated from polymers, other metals, metal alloys or semiconductor materials. The needle, for example, may be made of Parylene, silicon or glass. Microneedles and methods of fabrication are described in U.S. application Ser. No. 09/877,653, filed Jun.

8, 2001, entitled "Microfabricated Surgical Device", the entire disclosure of which is incorporated herein by reference.

Figure 3:
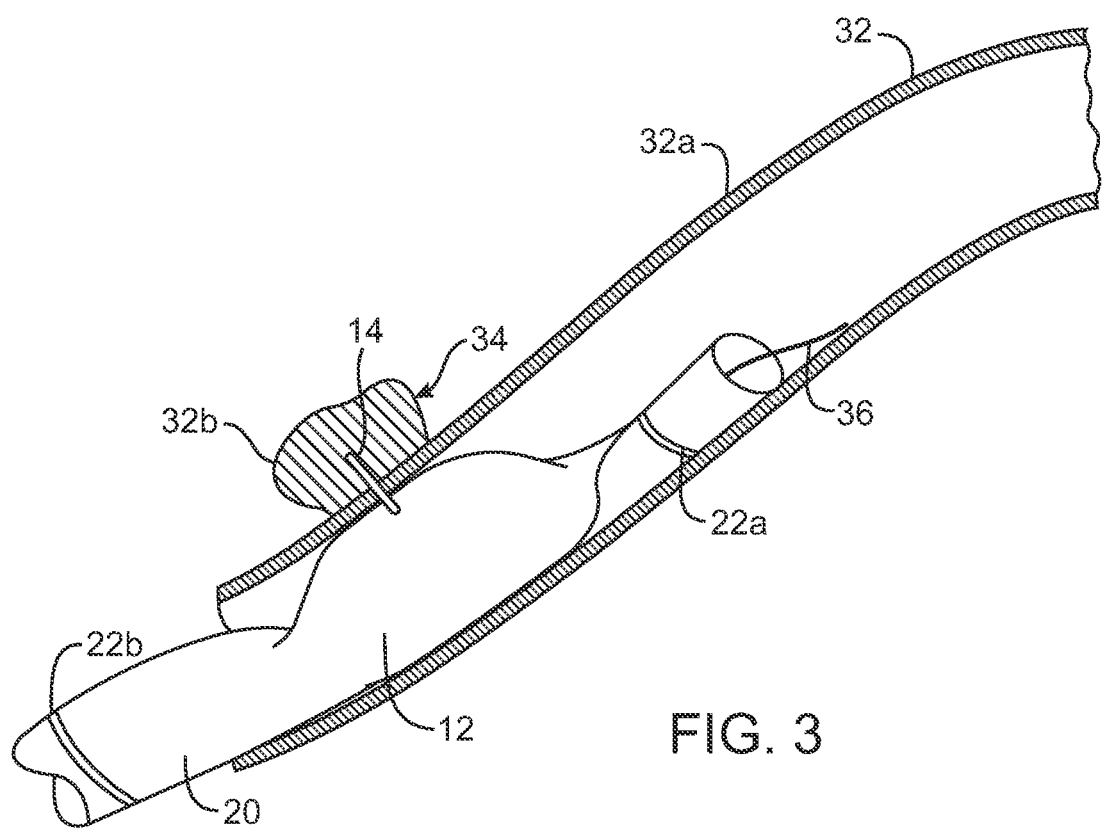

The catheter 20, in use, is inserted through an opening in the body (e.g. for bronchial or sinus treatment) or through a percutaneous puncture site (e.g. for artery or venous treatment) and moved within a patient's body passageways 32, until a specific, targeted region 34 is reached (see FIG. 3). The targeted region 34 may be the site of tissue damage or more usually will be adjacent the sites typically being within 100 mm or less to allow migration of the therapeutic or diagnostic agent. As is well known in catheter-based interventional procedures, the catheter 20 may follow a guide wire 36 that has previously been inserted into the patient. Optionally, the catheter 20 may also follow the path of a previously-inserted guide catheter (not shown) that encompasses the guide wire.

During maneuvering of the catheter 20, well-known methods of X-ray fluoroscopy or magnetic resonance imaging (MRI) can be used to image the catheter and assist in positioning the actuator 12 and the microneedle 14 at the target region. As the catheter is guided inside the patient's body, the microneedle remains furled or held inside the actuator body so that no trauma is caused to the body lumen walls.

After being positioned at the target region 34, movement of the catheter is terminated and the activating fluid is supplied to the open area 26 of the actuator, causing the expandable section 24 to rapidly unfurl, moving the microneedle 14 in a substantially perpendicular direction, relative to the longitudinal central axis 12$b$ of the actuator body 12$a$, to puncture a body lumen wall 32$a$. It may take only between approximately 100 milliseconds and five seconds for the microneedle to move from its furled state to its unfurled state.

The microneedle aperture, may be designed to enter body lumen tissue 32$b$ as well as the adventitia, media, or intima surrounding body lumens. Additionally, since the actuator is "parked" or stopped prior to actuation, more precise placement and control over penetration of the body lumen wall are obtained.

After actuation of the microneedle and delivery of the agents to the target region via the microneedle, the activating fluid is exhausted from the open area 26 of the actuator, causing the expandable section 24 to return to its original, furled state. This also causes the microneedle to be withdrawn from the body lumen wall. The microneedle, being withdrawn, is once again sheathed by the actuator.

Various microfabricated devices can be integrated into the needle, actuator and catheter for metering flows, capturing samples of biological tissue, and measuring pH. The device 10, for instance, could include electrical sensors for measuring the flow through the microneedle as well as the pH of the neuromodulating being deployed. The device 10 could also include an intravascular ultrasonic sensor (IVUS) for locating vessel walls, and fiber optics, as is well known in the art, for viewing the target region. For such complete systems, high integrity electrical, mechanical and fluid connections are provided to transfer power, energy, and neuromodulatings or biological agents with reliability.

By way of example, the microneedle may have an overall length of between about 200 and 3,000 microns (μm). The interior cross-sectional dimension of the shaft 14$b$ and supply tube 14$d$ may be on the order of 20 to 250 um, while the tube's and shaft's exterior cross-sectional dimension may be between about 100 and 500 μm. The overall length of the actuator body may be between about 5 and 50 millimeters (mm), while the exterior and interior cross-sectional dimensions of the actuator body can be between about 0.4 and 4 mm, and 0.5 and 5 mm, respectively. The gap or slit through which the central section of the actuator unfurls may have a length of about 4-40 mm, and a cross-sectional dimension of about 50 μm to 4 mm. The diameter of the delivery tube for the activating fluid may be between 100 and 500 μm. The catheter size may be between 1.5 and 15 French (Fr).

Figure 4A:
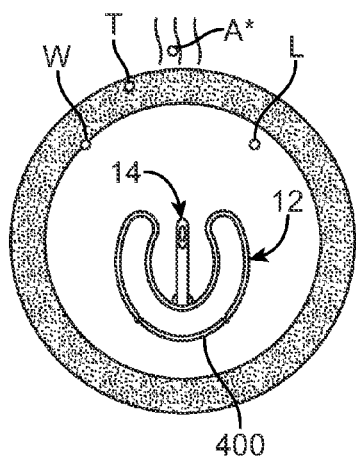

Referring to FIGS. 4A-4D, an elastomeric component is integrated into the wall of the intraluminal catheter of FIG. 1-3. In FIG. 4A-D, the progressive pressurization of such a structure is displayed in order of increasing pressure. In FIG. 4A, the balloon is placed within a body lumen L. The lumen wall W divides the lumen from periluminal tissue T, or adventitia A*, depending on the anatomy of the particular lumen. The pressure is neutral, and the non-distensible structure forms a U-shaped involuted balloon 12 similar to that in FIG. 1 in which a needle 14 is sheathed. While a needle is displayed in this diagram, other working elements including cutting blades, laser or fiber optic tips, radiofrequency transmitters, or other structures could be substituted for the needle. For all such structures, however, the elastomeric patch 400 will usually be disposed on the opposite side of the involuted balloon 12 from the needle 14.

Figure 4B:
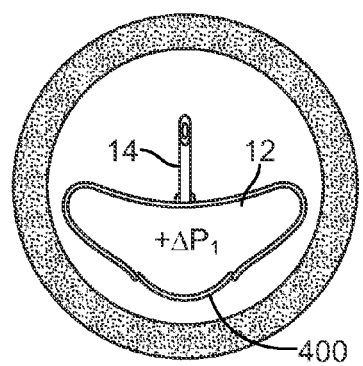
Figure 4C:
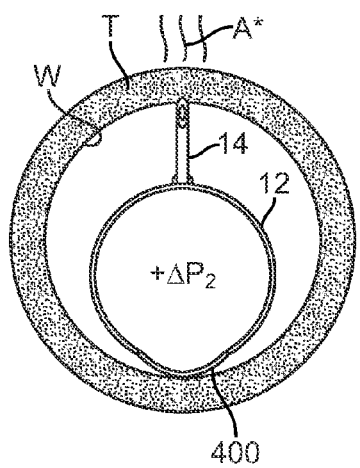
Figure 4D:
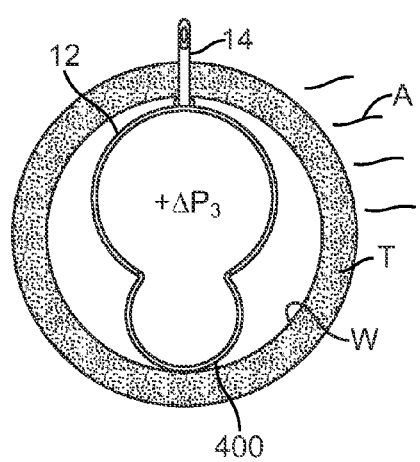

Actuation of the balloon 12 occurs with positive pressurization. In FIG. 4B, pressure ($+\Delta P_1$) is added, which begins to deform the flexible but relatively non-distensible structure, causing the balloon involution to begin its reversal toward the lower energy state of a round pressure vessel. At higher pressure $+\Delta P_2$ in FIG. 4C, the flexible but relatively non-distensible balloon material has reached its rounded shape and the elastomeric patch has begun to stretch. Finally, in FIG. 4D at still higher pressure $+\Delta P_3$, the elastomeric patch has stretched out to accommodate the full lumen diameter, providing an opposing force to the needle tip and sliding the needle through the lumen wall and into the adventitia A. Typical dimensions for the body lumens contemplated in this figure are between 0.1 mm and 50 mm, more often between 0.5 mm and 20 mm, and most often between 1 mm and 10 mm. The thickness of the tissue between the lumen and adventitia is typically between 0.001 mm and 5 mm, more often between 0.01 mm and 2 mm and most often between 0.05 mm and 1 mm. The pressure $+\Delta P$ useful to cause actuation of the balloon is typically in the range from 0.1 atmospheres to 20 atmospheres, more typically in the range from 0.5 to 20 atmospheres, and often in the range from 1 to 10 atmospheres.

Figure 5A:
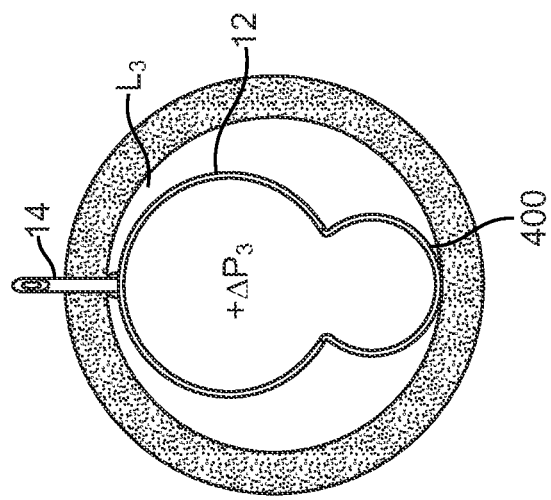
Figure 5B:
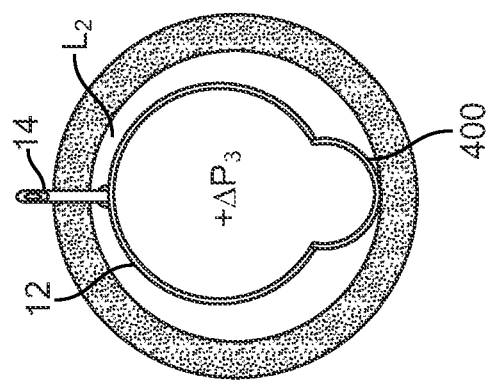
Figure 5C:
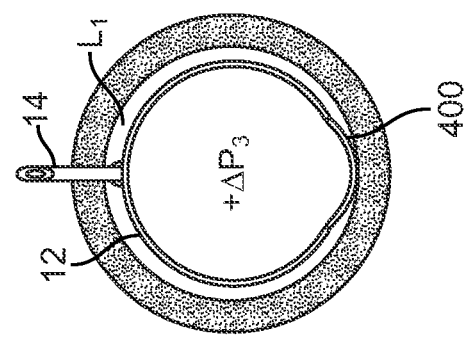

As illustrated in FIGS. 5A-5C, the dual modulus structure shown in FIGS. 4A-4D provides for low-pressure (i.e., below pressures that may damage body tissues) actuation of an intraluminal medical device to place working elements such as needles in contact with or through lumen walls. By inflation of a constant pressure, and the elastomeric material will conform to the lumen diameter to provide full apposition. Dual modulus balloon 12 is inflated to a pressure $+\Delta P_3$ in three different lumen diameters in FIGS. 5A, 5B, and 5C for the progressively larger inflation of patch 400 provides optimal apposition of the needle through the vessel wall regardless of diameter. Thus, a variable diameter system is created in which the same catheter may be employed in lumens throughout the body that are within a range of diameters. This is useful because most medical products are limited to very tight constraints (typically within 0.5 mm) in which lumens they may be used. A system as described in this invention may accommodate several millimeters of variability in the luminal diameters for which they are useful.

The above catheter designs and variations thereon, are described in published U.S. Pat. Nos. 6,547,803; 6,860,867; 7,547,294; 7,666,163 and 7,691,080, the full disclosures of which are incorporated herein by reference. Co-pending application Ser. No. 10/691,119, assigned to the assignee of the present application, describes the ability of substances delivered by direct injection into the adventitial and pericardial tissues of the heart to rapidly and evenly distribute within the heart tissues, even to locations remote from the site of injection. The full disclosure of that co-pending application is also incorporated herein by reference. An alternative needle catheter design suitable for delivering the therapeutic or diagnostic agents of the present invention will be described below. That particular catheter design is described and claimed in U.S. Pat. No. 7,141,041, the full disclosure of which is incorporated herein by reference.

Figure 6:
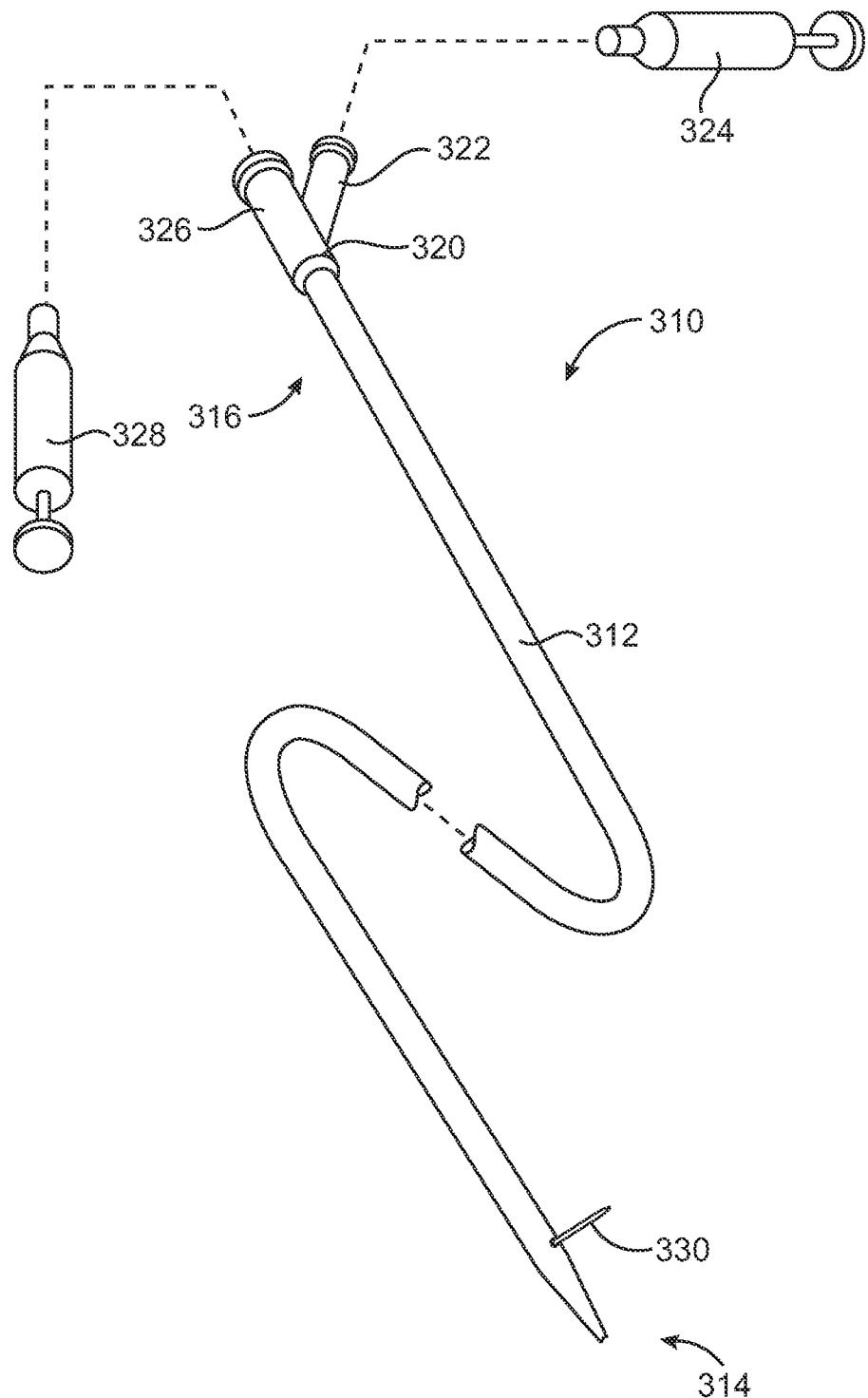

Referring now to FIG. 6, a needle injection catheter 310 constructed in accordance with the principles of the present invention comprises a catheter body 312 having a distal end 314 and a proximal 316. Usually, a guide wire lumen 313 will be provided in a distal nose 352 of the catheter, although over-the-wire and embodiments which do not require guide wire placement will also be within the scope of the present invention. A two-port hub 320 is attached to the proximal end 316 of the catheter body 312 and includes a first port 322 for delivery of a hydraulic fluid, e.g., using a syringe 324, and a second port 326 for delivering the neuromodulating agent, e.g., using a syringe 328. A reciprocatable, deflectable needle 330 is mounted near the distal end of the catheter body 312 and is shown in its laterally advanced configuration in FIG. 6.

Figure 7:
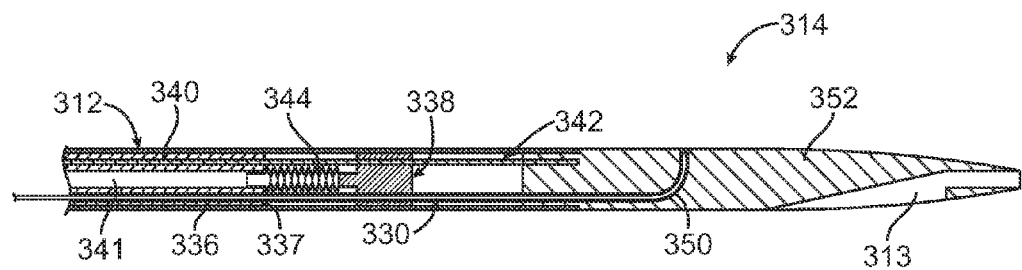

Referring now to FIG. 7, the proximal end 314 of the catheter body 312 has a main lumen 336 which holds the needle 330, a reciprocatable piston 338, and a hydraulic fluid delivery tube 340. The piston 338 is mounted to slide over a rail 342 and is fixedly attached to the needle 330. Thus, by delivering a pressurized hydraulic fluid through a lumen 341 tube 340 into a bellows structure 344, the piston 338 may be advanced axially toward the distal tip in order to cause the needle to pass through a deflection path 350 formed in a catheter nose 352.

Figure 8:
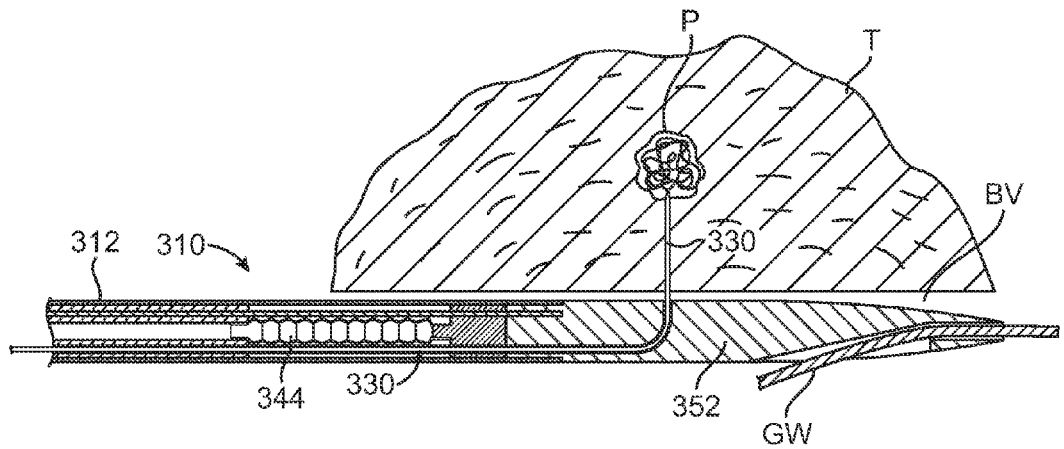

As can be seen in FIG. 8, the catheter 310 may be positioned in a blood vessel BV, over a guide wire GW in a conventional manner. Distal advancement of the piston 338 causes the needle 330 to advance into tissue T surrounding the lumen adjacent to the catheter when it is present in the blood vessel. The therapeutic or diagnostic agents may then be introduced through the port 326 using syringe 328 in order to introduce a plume P of agent in the cardiac tissue, as illustrated in FIG. 8. The plume P will be within or adjacent to the region of tissue damage as described above.

The needle 330 may extend the entire length of the catheter body 312 or, more usually, will extend only partially into the therapeutic or diagnostic agents delivery lumen 337 in the tube 340. A proximal end of the needle can form a sliding seal with the lumen 337 to permit pressurized delivery of the agent through the needle.

The needle 330 will be composed of an elastic material, typically an elastic or super elastic metal, typically being nitinol or other super elastic metal. Alternatively, the needle 330 could be formed from a non-elastically deformable or malleable metal which is shaped as it passes through a deflection path. The use of non-elastically deformable metals, however, is less preferred since such metals will generally not retain their straightened configuration after they pass through the deflection path.

The bellows structure 344 may be made by depositing by parylene or another conformal polymer layer onto a mandrel and then dissolving the mandrel from within the polymer shell structure. Alternatively, the bellows 344 could be made from an elastomeric material to form a balloon structure. In a still further alternative, a spring structure can be utilized in, on, or over the bellows in order to drive the bellows to a closed position in the absence of pressurized hydraulic fluid therein.

After the therapeutic material is delivered through the needle 330, as shown in FIG. 8, the needle is retracted and the catheter either repositioned for further agent delivery or withdrawn. In some embodiments, the needle will be retracted simply by aspirating the hydraulic fluid from the bellows 344. In other embodiments, needle retraction may be assisted by a return spring, e.g., locked between a distal face of the piston 338 and a proximal wall of the distal tip 352 (not shown) and/or by a pull wire attached to the piston and running through lumen 341.

Figure 9:
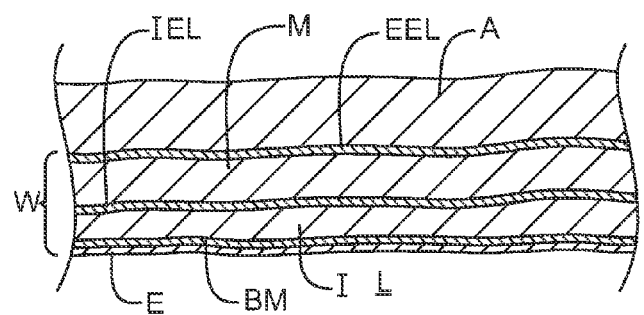

The perivascular space is the potential space over the outer surface of a "vascular wall" of either an artery or vein. Referring to FIG. 9, a typical arterial wall is shown in cross-section where the endothelium E is the layer of the wall which is exposed to the blood vessel lumen L. Underlying the endothelium is the basement membrane BM which in turn is surrounded by the intima I. The intima, in turn, is surrounded by the internal elastic lamina IEL over which is located the media M. In turn, the media is covered by the external elastic lamina (EEL) which acts as the outer barrier separating the arterial wall, shown collectively as W, from the adventitia layer A. Usually, the perivascular space will be considered anything lying beyond the external elastic lamina EEL, including regions within the adventitia and beyond.

Figure 10A:
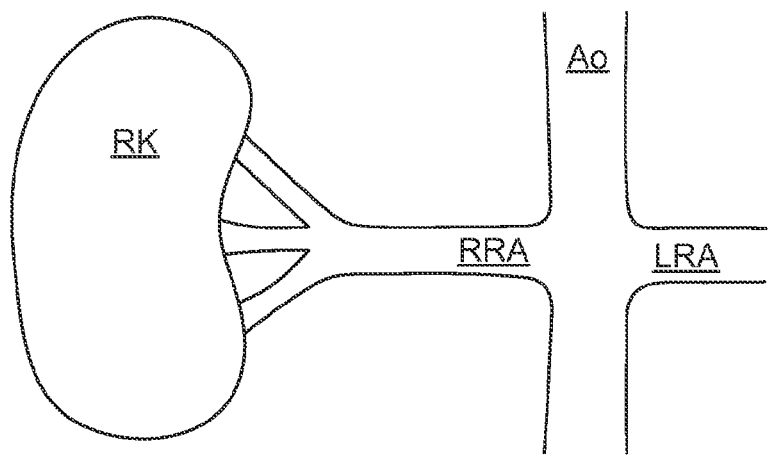
FIG. 10C is a cross-sectional view along line 10C-10C of FIG. 10B.
Figure 10B:
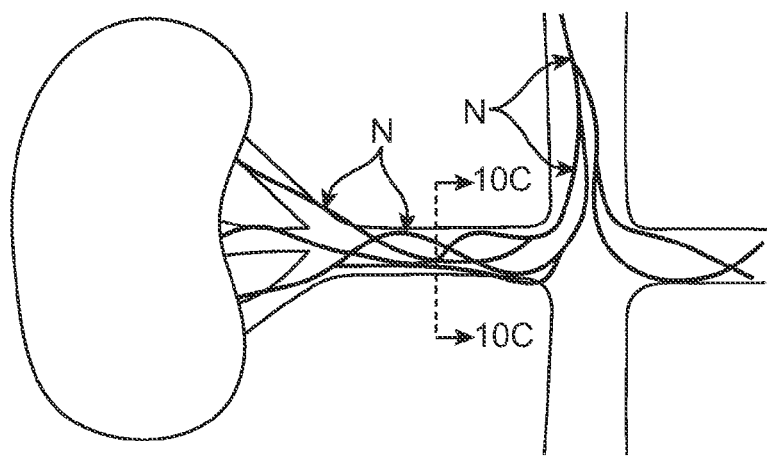
Figure 10C:
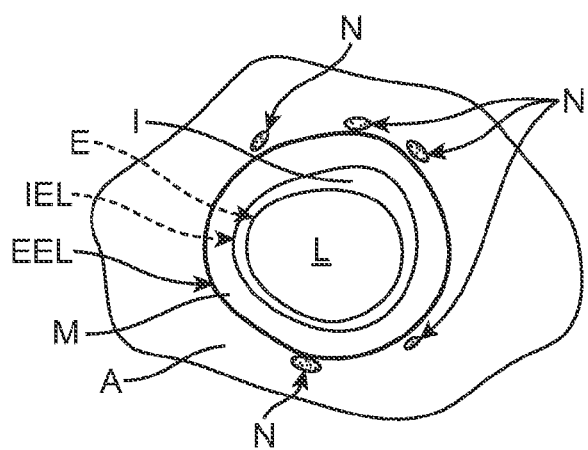

Turning now to FIG. 10A-C, the renal arterial location and structure are shown. In FIG. 10A, the aorta (Ao) is shown as the central artery of the body, with the right renal artery (RRA) and left renal artery (LRA) branching from the aorta to lead blood into the kidneys. For example, the right renal artery leads oxygenated blood into the right kidney (RK). In FIG. 10B, the nerves (N) that lead from the aorta to the kidney are displayed. The nerves are shown to surround the renal artery, running roughly parallel but along a somewhat tortuous and branching route from the aorta to the kidney. The cross-section along line 10C-10C of FIG. 10B is then shown in FIG. 10C. As seen in this cross-sectional representation of a renal artery, the nerves (N) that lead from aorta to kidney run through the arterial adventitia (A) and in close proximity but outside the external elastic lamina (EEL). The entire arterial cross section is shown in this FIG. 10C, with the lumen (L) surrounded by, from inside to outside, the endothelium (E), the intima (I), the internal elastic lamina (IEL), the media (M), the external elastic lamina (EEL), and finally the adventitia (A).

Figure 11A:
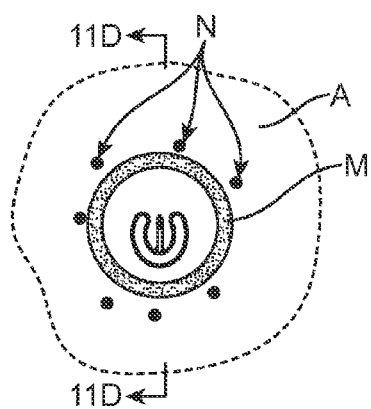
FIGS. 11A-11C are cross-sectional views similar to FIGS. 4A and 4D, shown with the injection needle advanced into the adventitia for progressive delivery of agents to sympathetic nerves according to the present invention.
Figure 11D:
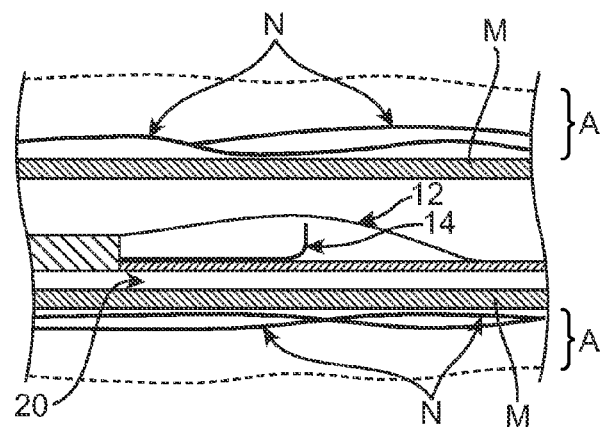
FIG. 11D is a cross-sectional view along line 11D-11D of FIG. 11A.

As illustrated in FIG. 11A-F, the methods of the present invention may be used to place an injection or infusion catheter similar to those illustrated by FIGS. 1-5 into a vessel as illustrated in FIG. 10C and to inject a plume (P) of neuromodulating agent into the adventitia (A) such that the agent comes in contact with the nerves (N) that innervate the adventitia of the renal artery. As can be seen in FIG. 11A, a catheter in the same state as FIG. 4A, wherein an actuator is shielding a needle so that the actuator can be navigated through the vessels of the body without scraping the needle against the vessel walls and causing injury, is inserted into an artery that has a media (M), an adventitia (A), and nerves (N) within the adventitia and just outside the media. A cross-section along line 11D-11D from FIG. 11A is shown in FIG. 11D. It can be seen from this cross section that a therapeutic instrument comprised similarly to those in FIGS. 1-3, with an actuator (12) attached to a catheter (20) and a needle (14) disposed within the actuator.

Figure 11B:
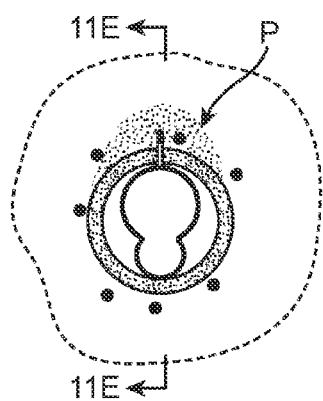
Figure 11E:
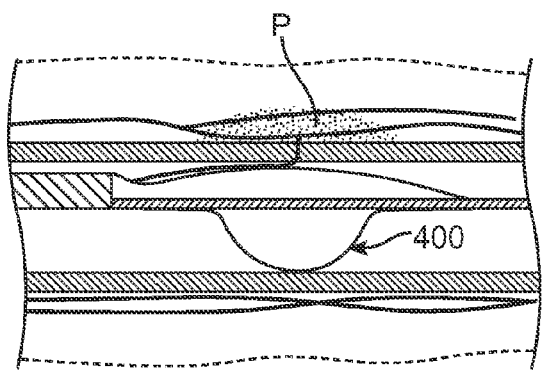
FIG. 11E is a cross-sectional view along line 11E-11E of FIG. 11B.

Turning to FIGS. 11B and 11E, we see the same system as that in FIGS. 11A and 11D, again where FIG. 11E is a view of the cross-section along line 11E-11E from FIG. 11B. In FIGS. 11B and 11E, however, the actuator that has been filled with a fluid, causing the actuator to unfurl and expand, and the needle aperture to penetrate the media and into the adventitia where nerves are located. After the needle penetrates to the adventitia, a plume (P) that consists of either diagnostic agent such as radio-opaque contrast medium or neuromodulating agent such as botulinum toxin or guanethidine or a combination of the diagnostic and therapeutic agents is delivered beyond the EEL and into the adventitia. The plume (P) begins to migrate circumferentially and longitudinally within the adventitia and begins to come into contact with the nerve fibers that run through the adventitia. At this point, the physician may begin to notice the therapeutic effects. Usually, the plume P that is used to diagnose the presence of the injection and the location of the injection is in the range from 10 to 100 µl, more often around 50 µl. The plume will usually indicate one of four outcomes: (1) that the needle has penetrated into the adventitia and the plume begins to diffuse in a smooth pattern around and along the outside of the vessel, (2) that the plume follows the track of a sidebranch artery, in which case the needle aperture has been located into the sidebranch rather than in the adventitia, (3) that the plume follows the track of the artery in which the catheter is located, indicating that the needle has not penetrated the vessel wall and fluid is escaping back into the main vessel lumen, or (4) that a tightly constricted plume is forming and not diffusing longitudinally or cyndrically around the vessel, indicating that the needle aperture is located inward from the EEL and inside the media or intima. The plume is therefore useful to the operating physician to determine the appropriateness of continued injection versus deflation and repositioning of the actuator at a new treatment site.

Figure 11C:
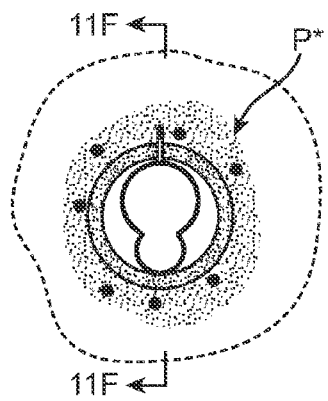
Figure 11F:
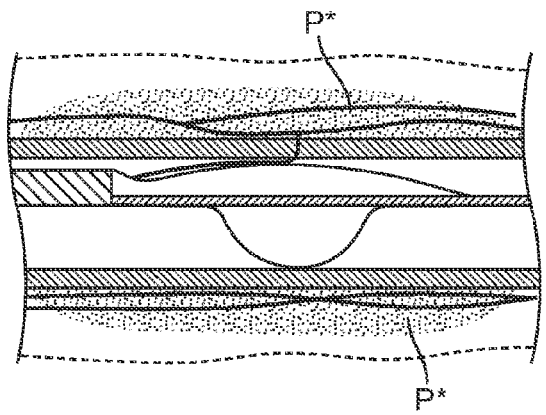
FIG. 11F is a cross-sectional view along line 11F-11F of FIG. 11C.

In FIGS. 11C and 11F, where FIG. 11F is a cross-sectional view across the line 11F-11F from FIG. 11C, one can see that after the plume is used to diagnose the appropriate tissue location of injection, further injection can be performed to surround the vessel with the neuromodulating agent. The extent of the final plume P* is usually fully circumferential around the artery and usually travels longitudinally by at least 1 cm when the injection volume is between 300 µl and 1 ml. In many cases, less than these volumes may be required in order to observe a therapeutic benefit to the patient's hypertension. At this point, the neuromodulating agent has penetrated the nerves around the entire artery, blocking the transmission of nerve signals and thereby creating chemical, neuromodulating, or biological denervation.

Figure 12:
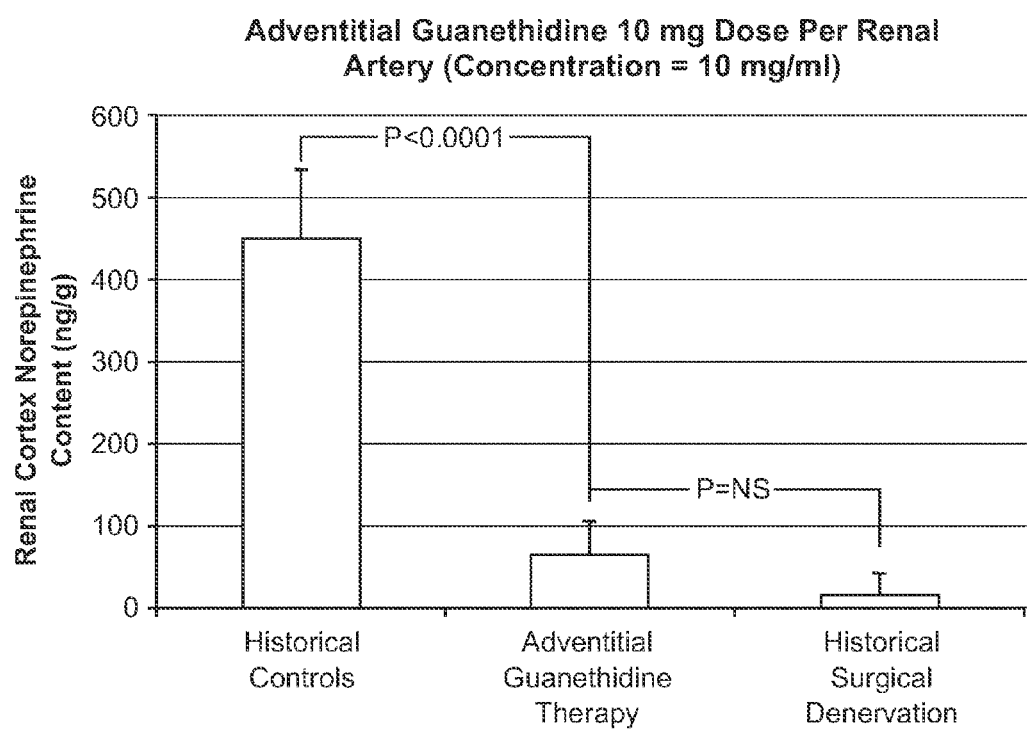
FIG. 12 is an illustration showing how botulinum toxin interacts with nerve cells to prevent the exocytosis of acetylcholine.

FIG. 12 illustrates the process by which botulinum toxin interrupts the transmission of nerve signals. In FIG. 12, it is seen that the toxin, here labeled "botulinum neurotoxin", is comprised of a "light chain" and a "heavy chain". The heavy chain is critical to bind the botulinum neurotoxin receptors and allow the botulinum neurotoxin to enter the cell by endocytosis. Once in the cell, the light chain of botulinum neurotoxin separates from the heavy chain in this illustration and cleaves SNARE proteins "syntaxin", "synaptobrefin", and "SNAP 25". When these SNARE proteins are cleaved, vesicles containing acetylcholine cannot be released from the nerve into the synaptic cleft. While this is shown in FIG. 12 for the neuromuscular junction, this is merely illustrative of the mechanism by which botulinum neurotoxin interacts with nerve cells, as it has also been shown that botulinum neurotoxins prohibit the release of acetylcholine and noradrenaline from other nerve junctions.

The following Experiments are offered by way of illustration, not by way of limitation.

EXPERIMENTAL

Studies were performed in a normal porcine model to determine if adventitial delivery of guanethidine could reduce kidney norepinephrine (NE), a marker for successful denervation. Successful denervation is well known to reduce blood pressure in hypertensive patients.

Renal denervation evidenced by NE reduction: Guanethidine monosulfate was diluted in 0.9% NaCl to a concentration of 12.5 mg/ml, then further diluted in iodinated contrast medium to a final concentration of 10 mg/ml. This solution was injected using a Mercator MedSystems Bullfrog Micro-Infusion Catheter (further described in this application and detailed in FIG. 11A-F) into the adventitia of both renal arteries, approximately halfway between the aorta and the hilum of the kidney. The injection was monitored with X-ray visualization of contrast medium to confirm adventitial distribution, which was confirmed to carry the injectate longitudinally and circumferentially around the artery, as well as transversely into the perivascular tissue. No injection was made into control animals, and historical controls from Connors 2004 were used as comparators.

Twenty-eight days after injection, kidneys and renal arteries were harvested. Kidney samples were taken using the method established by Connors 2004. Briefly, cortex tissue samples from the poles of the kidneys were removed and sectioned into approximately 100 mg segments. From each kidney, samples from each pole were pooled for analysis. Renal arteries were perfusion fixed in 10% neutral buffered formalin an submitted for histopathology.

Histology: Arteries appeared normal at 28 days, with no signs of vascular toxicity. Perivascular indications of denervation were apparent from lymphocyte, macrophage and plasma cell infiltration into adventitial nerve bodies, with nerve degeneration characterized by hypervacuolization and eosinophilia.

Figure 13:
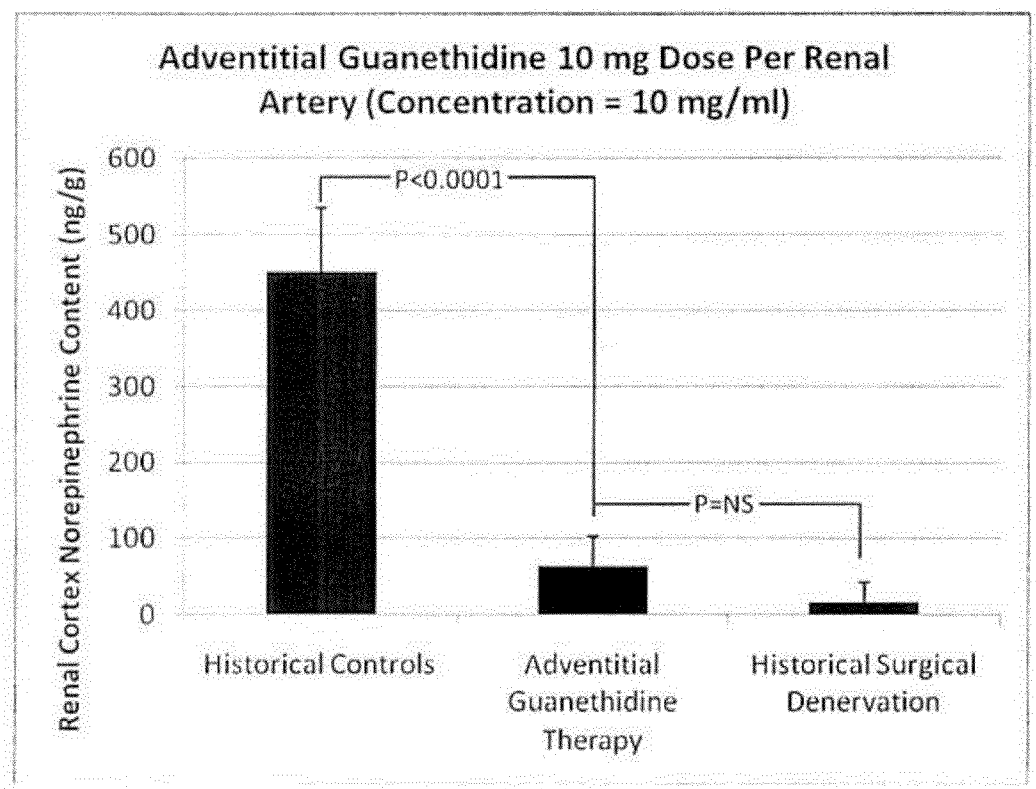
FIG. 13 is a graphical presentation of experimental data described herein.

Radio-immunoassay: NE levels in renal cortex tissue revealed average levels of 64 nanograms (ng) NE per gram (g) of renal cortex. When compared to normal controls of 450 ng/g, this represents a reduction in renal cortex NE of 86%. These data are shown in FIG. 13.

Additional comparison can be made to the reduction in renal cortex NE from surgical denervation, which Connors 2004 reported as 97% and Krum 2008 reported as 94%. Furthermore, the reduction in kidney NE reported with the use of radiofrequency catheter ablation of the renal nerves has been reported as 86%. The radiofrequency method has since been used in clinical trials and evidence has been shown that the ablation of the nerves, resulting in reduced NE by 86%, directly translates to reduced hypertension in patients, with reports of systolic pressure reduction of 27 mmHg and diastolic reduction of 17 mmHg, twelve months after treatment.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for treating hypertension in a subject, said method comprising the delivery of an amount of a neuromodulating agent to the nerves surrounding a blood vessel in a subject, wherein the amount is effective to lower systemic blood pressure by a therapeutically beneficial amount, and wherein delivery comprises injecting said agent into tissue bound on the inside by the external elastic lamina of said blood vessel and bound on the outside by the outer extent of the adventitial and perivascular connective tissues that surround the blood vessel.

2. A method as in claim 1, wherein delivery includes a step of positioning a needle through the wall of a target blood vessel so that an aperture of the needle is positioned beyond an external elastic lamina (EEL) of the wall.

3. A method as in claim 1, wherein delivery further includes a step of confirming that said neuromodulating agent is penetrating said tissue by imaging either the neuromodulating agent mixed with a diagnostic agent or by the delivery of a diagnostic agent prior to the delivery of the neuromodulating agent.

4. A method as in claim 1, wherein the blood vessel is an artery.

5. A method as in claim 4, wherein the artery is a renal artery.

6. A method as in claim 1, wherein the blood vessel is a vein.

7. A method as in claim 6, wherein the vein is a renal vein.

8. A method as in claim 1, wherein the neuromodulating agent is a neurotoxin or neurotoxin fragment.

9. A method as in claim 8, wherein the neurotoxin is a botulinum neurotoxin or fragment thereof.

10. A method as in claim 9, wherein the amount is between 10 picograms and 25 nanograms of active botulinum neurotoxin.

11. A method as in claim 9, wherein the amount is between 50 picograms and 10 nanograms of active botulinum neurotoxin.

12. A method as in claim 9, wherein the amount is between 100 picograms and 2.5 nanograms of active botulinum neurotoxin.

* * * * *